United States Patent [19]

Wissler

[11] Patent Number: 4,552,761
[45] Date of Patent: Nov. 12, 1985

[54] METHOD FOR INFLUENCING THE IMMUNE SYSTEMS OF MAMMALS USING LEUKORECRUITIN

[75] Inventor: Josef H. Wissler, Bad Nauheim, Fed. Rep. of Germany

[73] Assignee: Max-Planck Gesellschaft zur Forderung der/Wissenschaften, Gottingen, Fed. Rep. of Germany

[21] Appl. No.: 599,534

[22] Filed: Apr. 12, 1984

Related U.S. Application Data

[62] Division of Ser. No. 300,923, Sep. 10, 1981, Pat. No. 4,452,735.

[30] Foreign Application Priority Data

Sep. 12, 1980 [DE] Fed. Rep. of Germany ....... 3034529

[51] Int. Cl.$^4$ .............................................. C07G 7/00
[52] U.S. Cl. ................................ 424/101; 260/112 B; 260/112 R; 435/68; 435/69; 514/21; 514/885
[58] Field of Search ............................... 424/101, 177; 260/112 B, 112 R; 435/68, 69

[56] References Cited

PUBLICATIONS

Van Waarde, D. Blood, vol. 50, pp. 727–742, 1977.
Gordon, A. Annal New York Acad. Sci., 113, pp. 766–789, 1964.
Rother, K. Eur. J. Immunol., vol. 2, pp. 550–558, 1972.
Gerard, C., J. Biol. Chem., vol. 254, (Jul.), pp. 6346–6351, 1979.
Conroy, M., J. Immunol., vol. 116, pp. 1682–1687, 1976.
Wissler, J., Eurp. J. Immunol., vol. 2, pp. 73–96, 1972.
Ghebrehiwet B., J. of Immunol., vol. 123, pp. 616–621, 1979.

*Primary Examiner*—John Kight
*Assistant Examiner*—Nathan M. Nutter
*Attorney, Agent, or Firm*—Cooper, Dunham, Clark, Griffin & Moran

[57] ABSTRACT

The invention relates to SERUM-DERIVED "LEUKORECRUITIN", which is A PROTEIN MEDIATOR OF INFLAMMATION FROM MAMMALIAN SERUM specifically inducing positive leukocytosis reaction and leukocyte recruitment from the bone marrow into the blood of animals and humans without biological side-reactions. The process for the production and isolation of leukorecruitin is characterized in that mammalian serum is subjected to regulated and limited proteolysis by contact activation, the protein is then separated from other foreign constituents and proteins of serum in the form of a crude serum protein concentrate fraction, and/or the protein is separated from other serum-proteins by chromatography on hydroxy-apatite. Leukorecruitin has very valuable pharmacological effects and can be used in compositions for specifically influencing the defense state of the animal or human body and for diagnostic purposes in hematological disorders.

8 Claims, 15 Drawing Figures

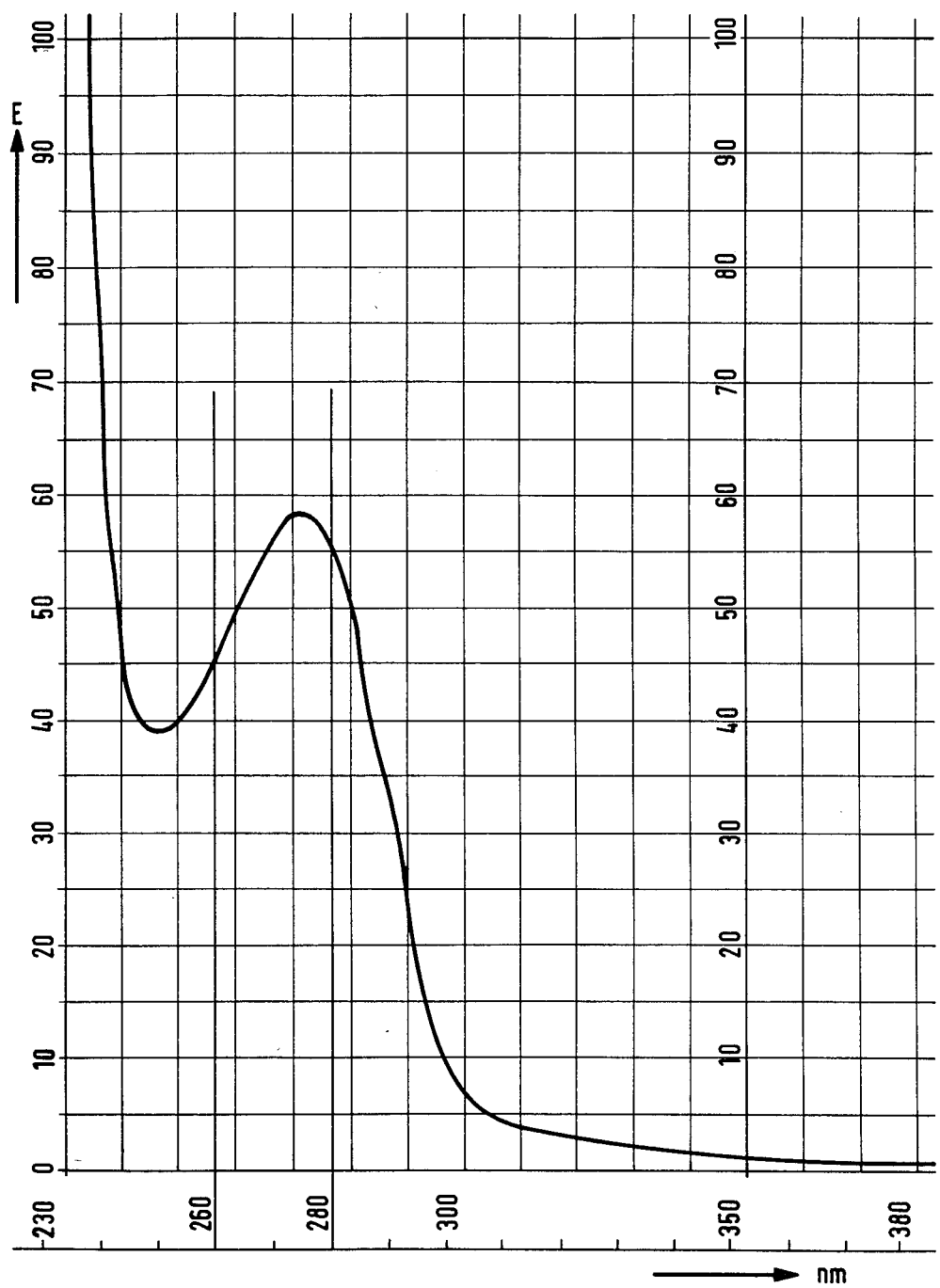
Fig. 1: ABSORPTION SPECTRUM OF LEUKORECRUITIN OF PORCINE SERUM DISSOLVED IN WATER AT 20°C. EXTINCTION SCALE (0-100) IS E = 0-2,0 AT d = 1 CM STANDARD PYROGEN ASSAY ACCORDING TO EUR. PHARMACOPOEIA 1975. RECTAL TEMPERATURE OF A RABBIT PRIOR TO (V,A), DURING (*) AND AFTER (P) INTRAVENOUS APPLICATION OF 1 μl (15 μg) LEUKORECRUITIN PER ANIMAL (≅ 0,63nmol/kg)

STANDARD PYROGEN ASSAY ACCORDING TO EUR. PHARMACOPOEIA 1975. RECTAL TEMPERATURE OF A RABBIT PRIOR TO (V,A), DURING (*) AND AFTER (P) INTRAVENOUS APPLICATION OF 1 µl (15 µg) LEUKORECRUITIN PER ANIMAL (≅ 0,63nmol/kg)

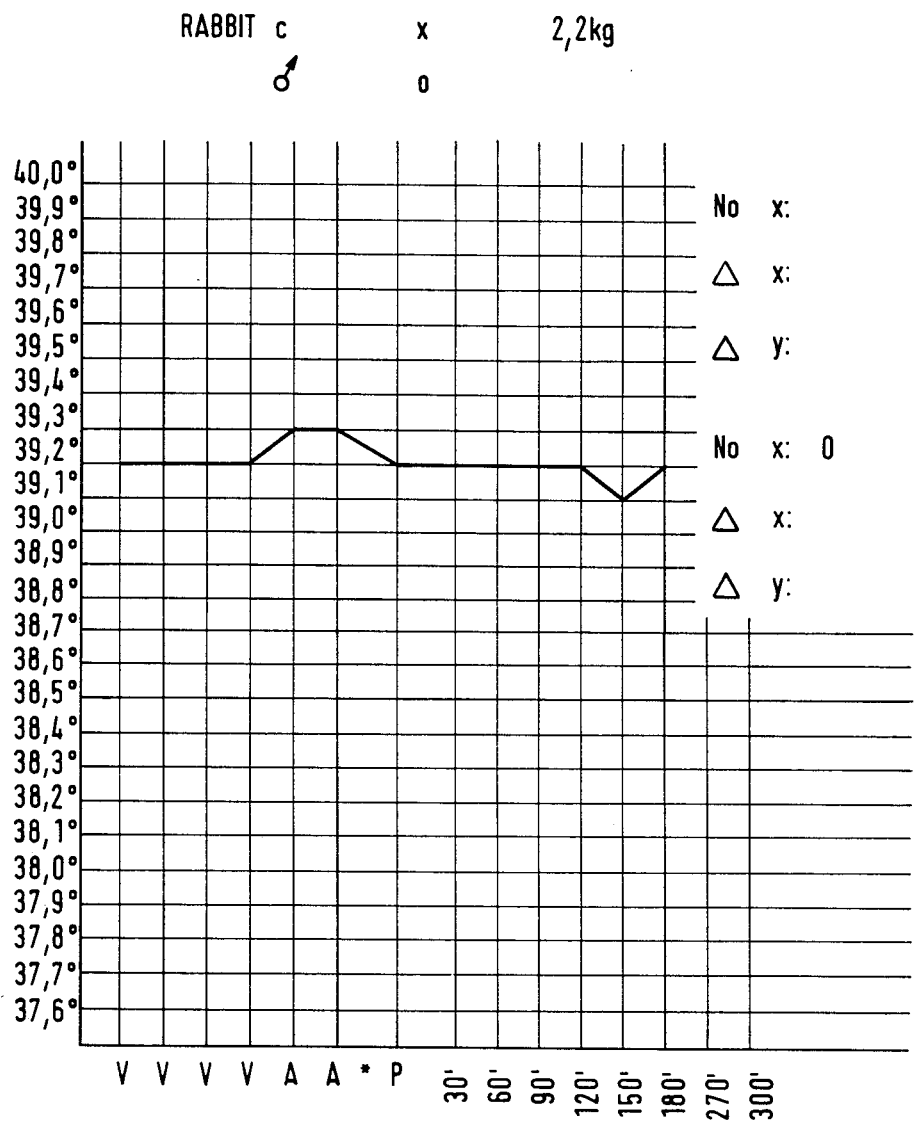
STANDARD PYROGEN ASSAY ACCORDING TO EUR. PHARMACOPOEIA 1975. RECTAL TEMPERATURE OF A RABBIT PRIOR TO (V,A), DURING (*) AND AFTER (P) INTRAVENOUS APPLICATION OF 1 μl (15 μg) LEUKORECRUITIN PER ANIMAL (≅ 0,63nmol/kg)

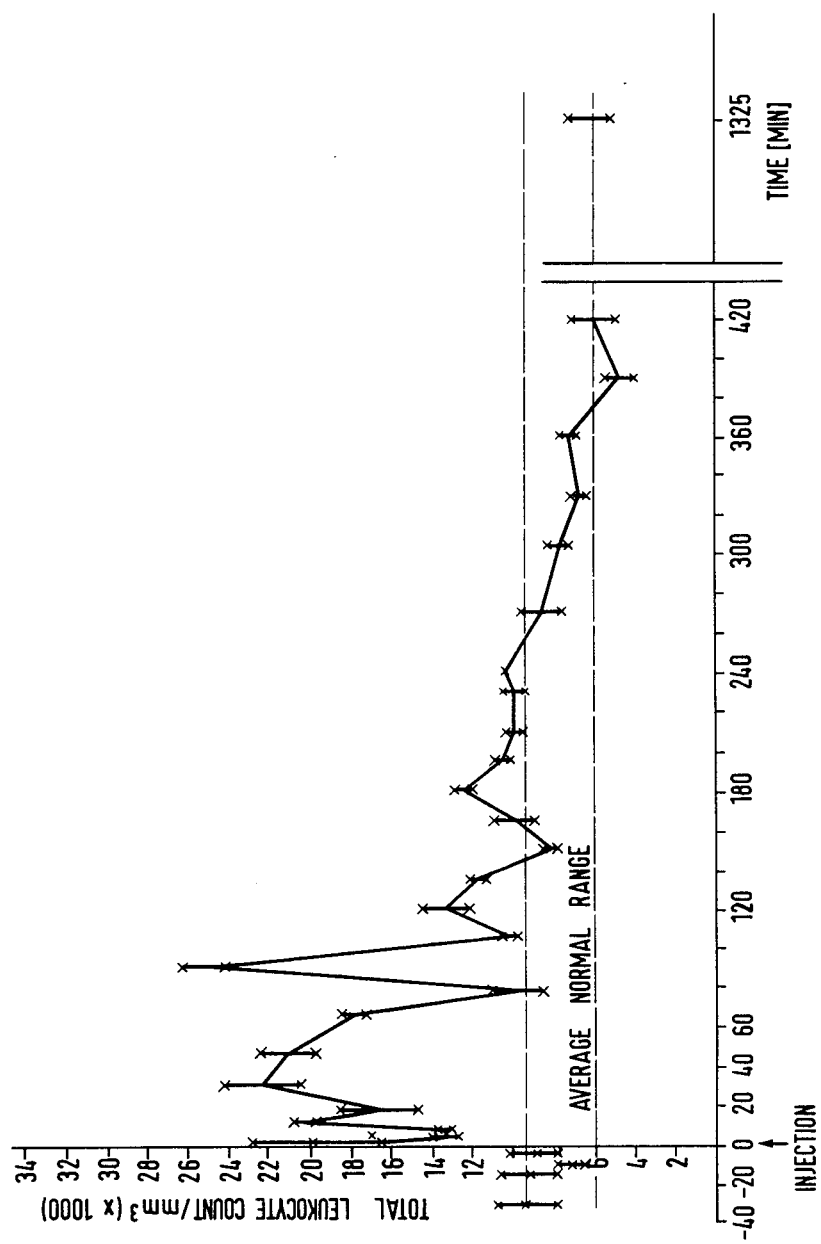

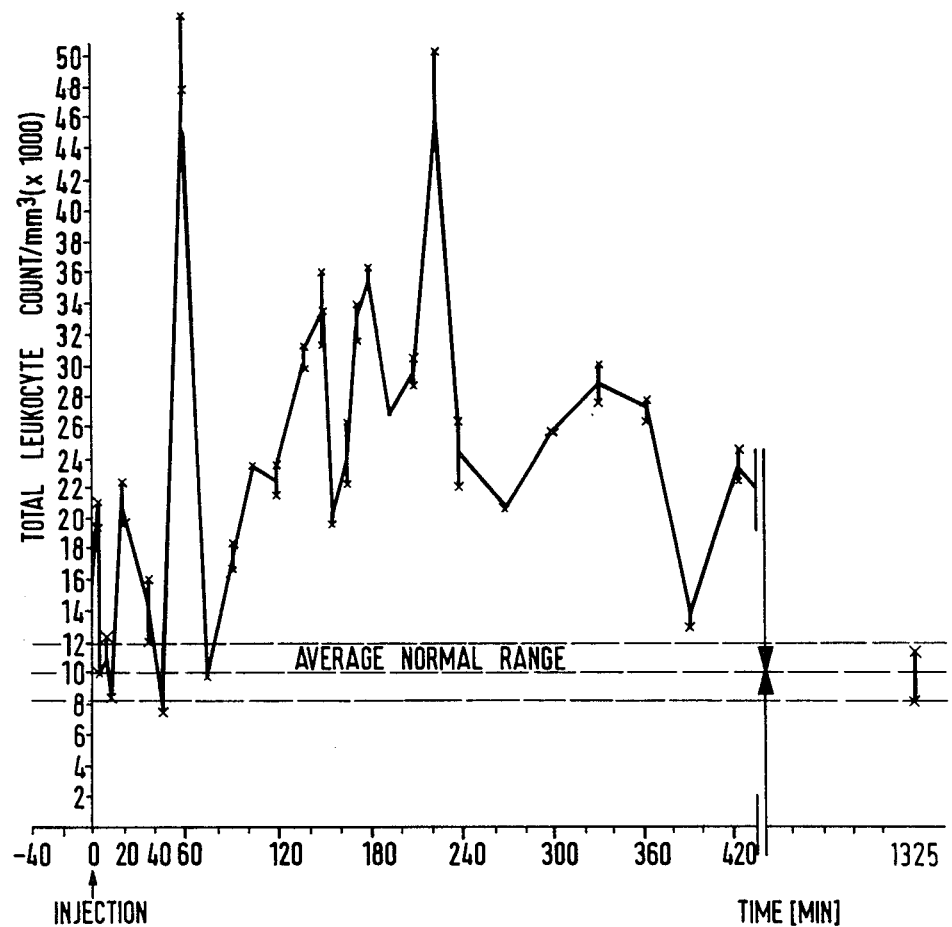
Fig. 4: LEUKOCYTOSIS REACTION UPON INTRAVENOUS ADMINISTRATION TO A GUINEA PIG OF 500 ng (60 p mol) OF HIGHLY PURIFIED MOLECULARLY HOMOGENEOUS LEUKORECRUITIN OF PROCIN SERUM PER KG GUINEA PIG

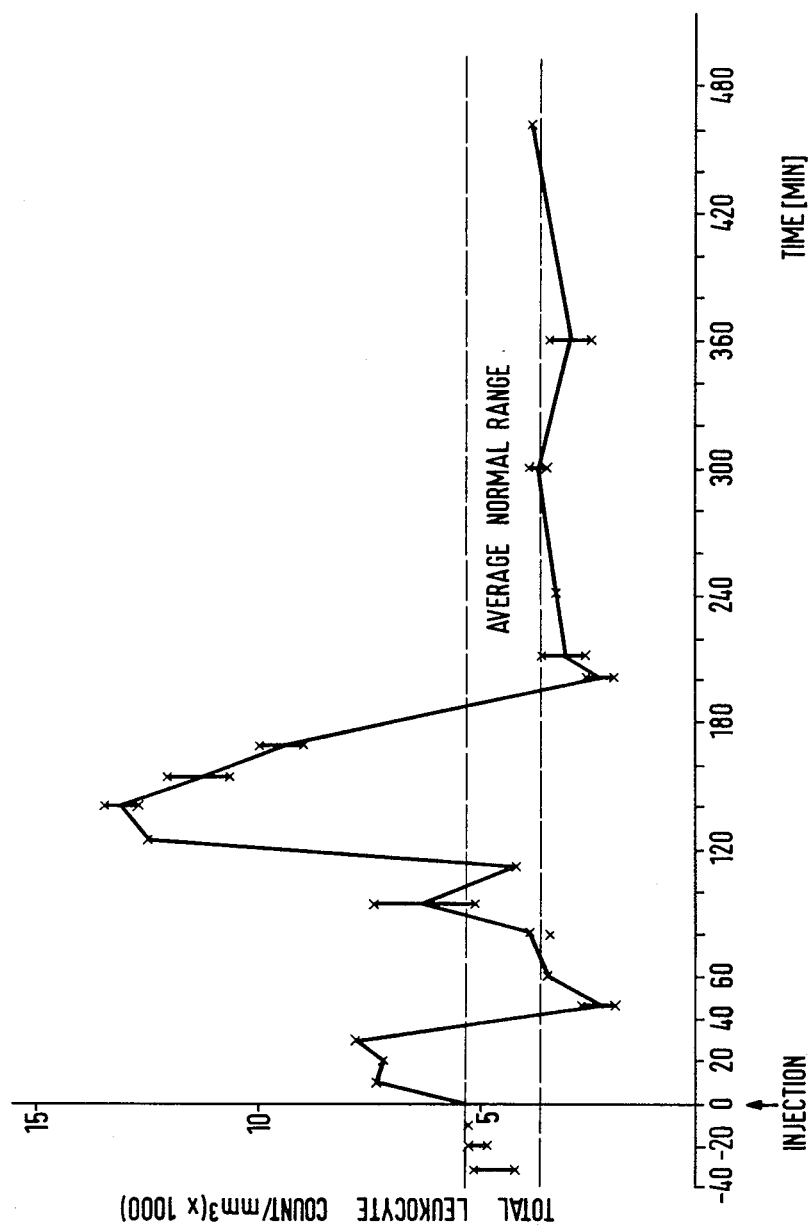

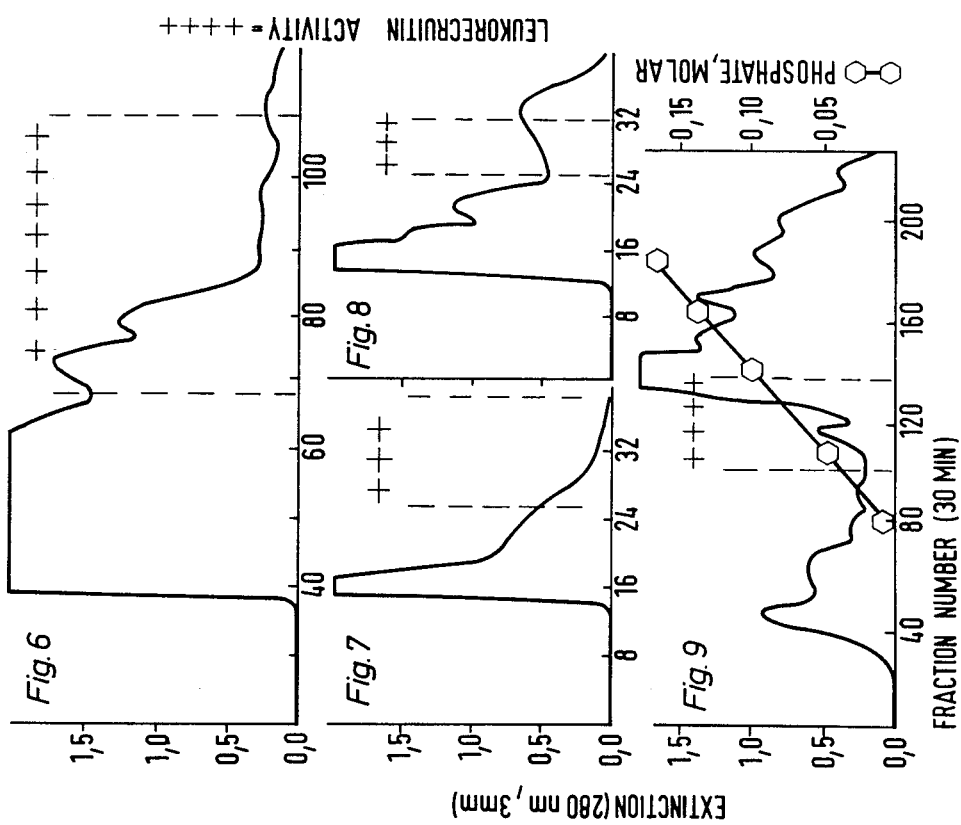

Fig. 6: EXAMPLE B6 FIRST PREPARATIVE MOLECULAR SIEVE FILTRATION OF THE CRUDE SERUM-PROTEIN CONCENTRATE FRACTION FROM EXAMPLE A

Fig. 7: EXAMPLE B6 SECOND PREPARATIVE MOLECULAR SIEVE FILTRATION OF THE LR-CONTAINING PROTEIN CONCENTRATE OF FIG. 6

Fig. 8: EXAMPLE B6 ANALYTICAL MOLECULAR SIEVE FILTRATION OF THE LR-CONTAINING CONCENTRATE OF FIG 7

Fig. 9: EXAMPLE C1 CHROMATOGRAPHY ON HYDROXYAPATITE OF THE LR-CONTAINING PROTEIN CONCENTRATE OF FIG. 8

CONTINUATION

FIG. 10: FINAL PURIFICATION OF THE LR

EXAMPLE C4
ANALYTICAL RECYCLING MOLECULAR SIEVE FILTRATION CHROMATOGRAPHY FOR FURTHER PURIFICATION OF THE LR FRACTION OBTAINED IN FIG. 9

CONTINUATION:
FINAL PURIFICATION SEQUENCE FOR THE LR FIG. 11 - 13

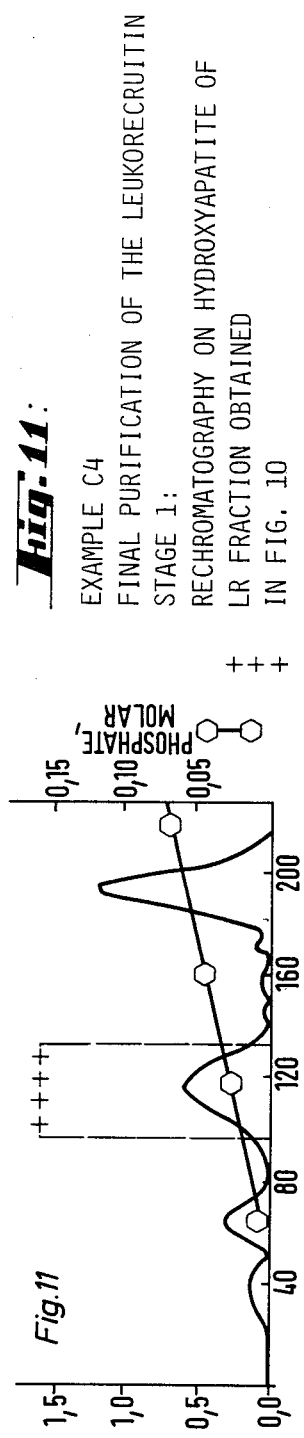

Fig. 11:

EXAMPLE C4
FINAL PURIFICATION OF THE LEUKORECRUITIN
STAGE 1:
RECHROMATOGRAPHY ON HYDROXYAPATITE OF
LR FRACTION OBTAINED
IN FIG. 10

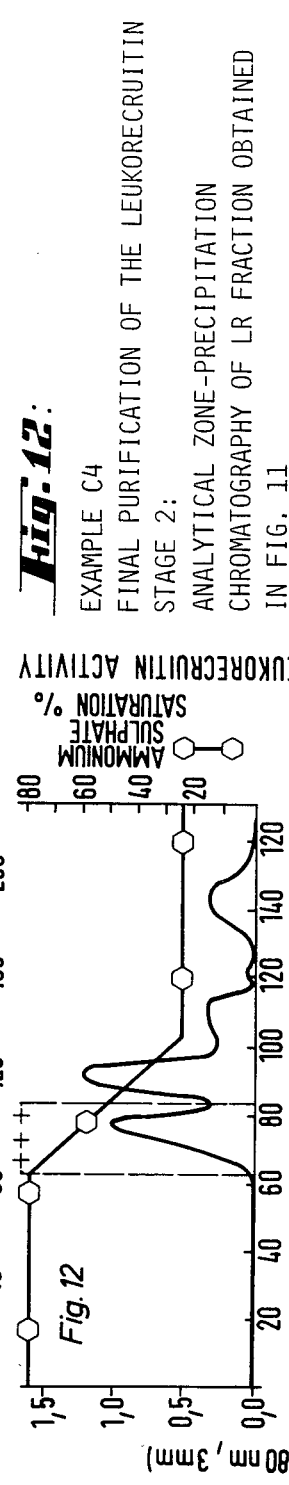

Fig. 12:

EXAMPLE C4
FINAL PURIFICATION OF THE LEUKORECRUITIN
STAGE 2:
ANALYTICAL ZONE-PRECIPITATION
CHROMATOGRAPHY OF LR FRACTION OBTAINED
IN FIG. 11

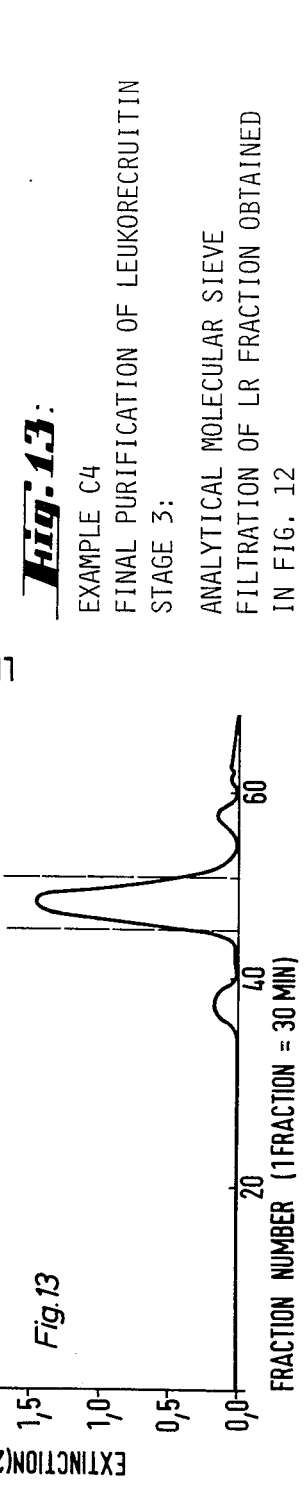

Fig. 13:

EXAMPLE C4
FINAL PURIFICATION OF LEUKORECRUITIN
STAGE 3:
ANALYTICAL MOLECULAR SIEVE
FILTRATION OF LR FRACTION OBTAINED
IN FIG. 12

METHOD FOR INFLUENCING THE IMMUNE SYSTEMS OF MAMMALS USING LEUKORECRUITIN

This is a division of application Ser. No. 300,923, filed Sept. 10, 1981, now U.S. Pat. No. 4,452,735.

BACKGROUND OF THE INVENTION

Degeneration of tissue, inflammation and wound healing induced by non-immunological and/or by immunological processes lead to the formation of a variety of endogenous, biologically active substances (mediators and hormones). Mostly, their nature and mode of action have not been characterized in detail so far. They regulate the complex individual steps of activation of inflammation and tissue repair processes and thus participate in homeostasis and turnover of tissues. Accumulation of leukocytes by chemoattraction, altered hemodynamics, smooth muscle contraction, fever, angiogenesis, leukocytosis, leukopenia and/or leftward shift reactions, but also shock symptoms, are examples of classical phenomena in physiopathology which can be mediator-induced and which are operative in and/or accompany systemic and local defense and repair mechanisms in inflammation, wound healing, tumor growth and reproductive cycles. These substances are produced either as humoral mediators by limited and regulated proteolysis of serum and plasma proteins; or they are released as cellular mediators from cells and tissues by cell lysis or active (autocrine, paracrine or endocrine) secretion. They form part of the body's defense system, the systemic and local activation of which they regulate. Thus, they contribute to removal and detoxification of destroyed endogenous substances and/or of invaded exogenous foreign bodies. In addition, by regulation of the cell-division and tissue growth processes in wound healing they participate in restoration of physiological structures and functions of the organism. Like the classical hormones of endocrine glands, inflammatory mediators are trace substances that are present in situ in very minute concentrations in tissue or blood. So far, however, once isolated in a biologically specific active form, they also can be considered and may be useful as ideal, valuable (natural) drugs of high specificity of action and lack of undesired side-effects (intrinsic to synthetic drugs), since they have been formed by, and underwent natural selection in evolution.

By activation of the kinin system, the coagulation system, the complement system and also of other blood protein and cell factors, a variety of humoral mediators may be produced concurrently or sequentially which are responsible for the numerous apparent biological activities of the activated serum. The leukocytosis reaction (reactive mobilization and recruitment of leukocytes from the bone marrow into the blood with reactive increase of blood cell number over normal level) is also such a mediator-triggered reaction. The recruitment of leukocytes from the bone marrow is a common feature of acute inflammatory processes, for example in bacterial infections or myocardial infarction. The leukocytosis reaction constitutes part of feed-back mechanism in regulatory loops of the body's defense system to maintain the structural and functional readiness of the organism for tissue repair. Hence impaired function in leukocyte mobilization mechanisms, e.g. in virus infections or genetic defects (congenital genetic agranulocytosis) may have fatal prognosis.

Two negative feedback mechanisms have been postulated for homeostasis (maintainance of the normal range) of constant blood leukocyte concentration. One shall be responsible for production of cells in the bone marrow and the other for their release into the blood; c.f. D. R. Boggs, Ann.Rev., Physiol., vol. 28 (1966) p. 39–56. Humoral mediators are thought to play a part in these regulatory loops; cf. V. Menkin, Biochemical Mechanisms in Inflammation, 2nd edition, Charles C. Thomas, Springfield, Illinois, 1956. In this work, Menkin also showed for the first time that soluble mediators are likewise involved in mechanisms, which increase the blood leukocyte concentration above the normal level range (leukocytosis reaction). He isolated a crystallizable protein-like material from inflammatory exudates which induced a leukocytosis reaction in vivo, but which was not identified and characterized in detail.

These early experiments provided a valuable basic knowledge of formation, nature and possible mode of action of inflammatory mediators. However, so far, on the one hand it was impossible to rule out possible contaminations of the material with bacterial endotoxins which may mimic non-specifically and indirectly through mediator formation the activities ascribed to the protein preparations [cf. D. R. Boggs, op. cit. (1966)]. On the other hand, it could not be excluded that contaminations with other trace proteins caused artefact reactions, since present methods for selective purification of complex mixtures and analysis of proteins for molecular homogeneity were not available at that time.

Many different factors can trigger leukocytosis reactions in the intact organism. Amongst them to mention are infections, immune reactions, mechanical tissue damage, drugs (e.g. cortisone, mental stress, or even the consumption of extensive meals. However, leukocytosis reaction may be induced when leukocytes are recruited from marginated (secondary) storage pools in tissues or from their production site, the bone marrow, which also constitutes a (primary) storage pool for leukocyte recruitment; cf. H. E. Whipple and M. I. Spitzer, Ann. N.Y. Acad. Sci. 113 (1964) pp. 511–1092. Hence, increase of blood leukocyte concentration (leukocytosis) is not simply identical to mobilization of leukocytes from bone marrow.

Whether or not such triggers act directly or indirectly (by formation of specific mediators) on the bone marrow and its leukocyte storage pools remained a matter of debate, and has to be established from case to case. A main indirect trigger in infections are endotoxins (lipopolysaccharides) which exert many biological effects by activating homoral (e.g. the serum complement system) and cellular defense system (e.g. B-lymphocytes, monocytes etc.). Thus, their indirect effects on hematopoesis earlier served as to assay them; cf. O. Lüderitz, Angew. Chem. 82, (1970), pp. 708–722. Hence, a main problem intrinsic to research in basic mechanisms of leukocyte mobilization from the bone marrow into blood circulation, thus, was the development of reliable in-vitro test systems, the results of which can be correlated to in-vivo leukocytosis reaction test systems. A. S. Gordon et al. [Ann. N.J. Acad. Sci., vol. 113 (1964) p. 766–789] developed such a laborious in-vitro test system with which they obtained a leukocytosis-inducing plasma factor. Its nature has not been clarified in greater detail, and its function rather must be considered as part of the feed-back mechanisms that might correct reduced blood leukocyte concentrations (leukopenia) to normal levels.

K. Rother [Eur. J. Immunol., vol. 2 (1972), pp. 550–558] developed another reliable, but less laborious in-vitro test system for the detection of leukocyte mobilization from the bone marrow. Rother was the first to put forward the argument that a humoral factor from the third component of the complement system plays a part in the leukocytosis reaction. This finding led to protein preparations, the nature, molecular homogeneity and/or biological specificity of which, however, were not further characterized in detail. In addition, their preparation methods were not considered for obtaining physical quantities for use in practice of a mediator of the leukocytosis reaction. Recent experience with inflammatory mediators shows [cf. J. H. Wissler, Eur. J. Immunol., vol. 2 (1972), pp. 73–96] that these are trace substances active in the nanomolar concentration range. Hence, for their preparation in molecularly homogenous form and in physical quantities, purification techniques used in multi-step sequences are necessary which can easily handle large volumes of the starting material.

For example, one of these protein preparations was obtained by activation of the serum complement system in small volumes of serum of small animals followed by a sequence of steps of fractional salting-out precipitation with ammonium sulfate, an electrophoresis and a molecular sieve chromatography; cf. K. Rother op. cit. This protein preparation induces the release of leukocytes from an isolated rat femur in vitro and a leukcytosis reaction in vivo. The in vivo leukocytosis reaction seems to be complex. It is biphasic and can be inhibited only in part by an antibody serum preparation to the complement component C3; [cf. K. Rother et al., Z. Immun.-Forsch.-Immunobiology, vol. 155 (1978), p. 55].

A similar protein preparation (molecular weight 10,000 to 12,000 dalton) has been prepared by B. Ghebrehiwet and J. H. Müller-Eberhard, J. Immunol., vol. 123 (1979), pp. 616–621, by digestion with trypsin of a preparation of complement component C3. This preparation was purified by electrophoresis or alternatively by means of an ion exchange step and electrophoresis. The protein preparation contains no tyrosine as amino acid structural component; cf. B. Ghebrehiwet and J. H. Müller-Eberhard, op.cit. (1979). It mobilizes leukocytes in vitro and induced a leukocytosis reaction in rabbits in vivo with a specific activity of 10 µg/kg (1 mol/kg). In addition, it was found that this preparation acts nonspecifically and has more than one biological activity: It also increases capillary permeability in situ and exerts a local phlogistic action (emigration of leukocytes into the tissue); cf. B. Ghebrehiwet and J. H. Müller-Eberhard, op.cit. (1979).

A different biologically active factor inducing a very late monocytosis reaction (after 24–48 hours) without affecting granulocyte levels in mice has been detected in murine serum during the early phase of an inflammatory reaction, having a molecular weight of 18,000 to 24,000 dalton; [cf. D. van Waarde et al., Blood, vol. 50 (1977), pp. 727–742]. Whether or not this factor is derived from serum proteins or is of cellular origin has not been clarified and its purification and further characterization waits to be established.

Measurement of leukocyte mobilization from the bone marrow and leukocyte recruitment into blood on the one hand is carried out biologically, either in vitro according to the test system of K. Rother (rat femur) [Eur. J. Immunol. vol. 2 (1972), pp. 550–558; or in vivo by time-dependent periodic counting and differentiation of the various types of leukocytes in the blood after administration of a solution of the substance under investigation. On the other hand, the leukorecruitin can be measured physico-chemically by the various usual immunochemical methods (e.g. immunodiffusion immunoelectrophoresis, or radioimmunoassay) using an anti-leukorecruitin immunoglobulin preparation. It can be prepared from the molecularly homogeneous, purified leukorecruitin in accordance with the invention. With these test systems leukocyte-recruiting activity can be discovered in serum or plasma after their activation by contact reactions with many high molecular, exogenous substances (such as immune complexes, endotoxins, or snake venoms), microorganisms (e.g., Pseudomonas), and proteolytic enzymes. Similiar findings have been obtained by K. Rother, op. cit (1972) and B. Ghebrehiwet and J. H. Müller-Eberhard, op. cit (1979). However, in certain cases long incubation periods (e.g. 5 days) are necessary.

It is therefore a primary object of this invention to provide a natural leukocytosis-inducing (leukocyte-recruiting and mobilizing) protein from mammalian serum.

It is another object of this invention to provide a natural leukocytosis-inducing protein from mammalian serum in molecularly homogeneous crystallizable form.

It is another object of this invention to provide a natural leukocytosis-inducing protein from mammalian serum, which represents a biologically specific, active and natural mediator of the leukocytosis reaction.

It is another object of this invention to provide a natural leukocytosis-inducing protein from mammalian serum, which is suitable for specifically influencing the defense state of mammalian (e.g. human) organism.

It is still another object of this invention to provide a process for producing and obtaining a natural leukocytosis-inducing protein from mammalian serum plasma or blood.

It is still another object of this invention to provide a process for producing and obtaining a natural leukocytosis-inducing protein from mammalian serum plasma or blood in an economical, biotechnically useful and relatively simple manner.

It is still another object of this invention to provide a process for producing and obtaining a natural leukocytosis-inducing protein from mammalian serum plasma or blood in a highly purified, molecularly homogeneous, crystallizable form and in physical quantities for practical use.

These and other objects and advantages of the present invention will be evident from the following description of the invention and the drawings.

BRIEF DESCRIPTION OF THE DRAWINGS

FIG. 1 graphically illustrates the adsorption spectrum (uv, visible and near IR region) of leukorecruitin prepared in accordance with this invention.

FIGS. 2a, 2b, 2c graphically illustrate the pyrogen assays of the materials of this invention upon the administration of a fixed amount thereof to rabbits.

FIGS. 3–5 graphically illustrate the leukocytosis reaction upon intravenous administration of varying amounts of the material of this invention to guinea pigs.

FIGS. 6–9 graphically illustrate the various preparatory procedures in connection with the multiple molecular sieve filtration of followed by chromatography for the concentration and purification of the materials to this invention.

FIGS. 11, 12 and 13 graphically illustrate sequentially the final various steps in the purification of the materials involving chromatography and molecular sieve filtration in accordance with this invention.

SUMMARY OF THE INVENTION

Figure 2A:
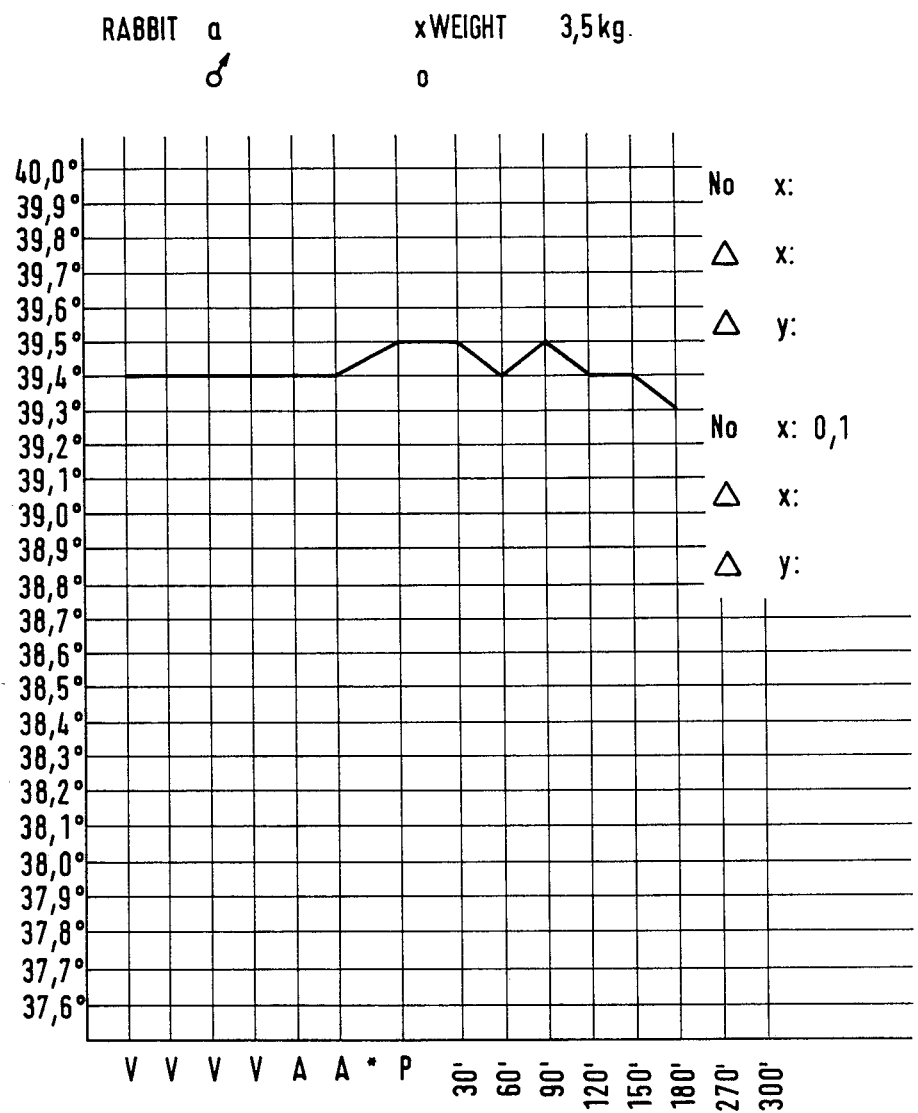

The subject matter of the invention is a natural leukocytosis-inducing (leukocyte-recruiting) protein (leukorecruitin), characterized by the following properties:

(a) biological effects in vivo and in vitro:
 positive leukocytosis reaction and leukocyte recruitment from the bone marrow into the blood of animals and humans in vivo;
 positive leukocyte mobilization directly from the bone marrow in vitro (also in blood-free systems such as cell culture and salt solution);
 it is substantially free of other biological effects.
(b) physico-chemical properties:
 it has typical protein properties and protein reactions (folin and biuret reactions);
 its melting point is about 200° C. (decomp. in an air and oxygen free atmosphere);
 the molecular weight of the native protein (primary structure): about 8500 dalton;
 it has no quaternary protein structure in the form of physically bound peptide sub-units: the native protein consists of only one peptide unit;
 its electrophoretic migration at pH 7.40 in acrylamide matrices is anodic;
 it is soluble in aqueous media including 20% of ethanol at a pH of at least 4.0 to 10;
 it is insoluble in $(NH_4)_2SO_4$ solutions at concentrations higher than 61% (2.50 mol $(NH_4)_2SO_4/l$) (salting-out precipitation of leukorecruitin);
 it has a constant temperature coefficient of solubility in ammonium sulfate solutions between $-10°$ C. and $+50°$ C.; it crystallizes in form of double-refractive, optically anisotropic crystals from ammonium sulfate solutions at ammonium sulfate concentrations higher than 61%; it is insoluble in chloroform, benzene, xylene, and other apolar, anhydrous solvents and water-immiscible solvents;
 it is denatured in chloroform, benzene, and xylene; destruction of conformation structure (secondary and tertiary structure) and of biological activity;
 it contains amongst others the amino acids tyrosine, tryptophan, phenylalanine, alanine, glycine, lysine, serine, valine, glutamic acid, arginine and leucine;
 absorption spectrum (UV, visible and rear IR region) as given in FIG. 1;
 extinction coefficients according to the following table (Table I):

TABLE I

| Wavelength, nm | $E_{1\ mg/ml,\ 1\ cm\ (H_2O,\ 20°\ C.)} \pm 6\%$ |
| --- | --- |
| 250 (min) | 0,36 |
| 260 | 0,42 |
| 277 (max) | 0,54 |
| 280 | 0,53 |
| 290 | 0,32 |
| 400 | 0 |
| 450 | 0 |

TABLE I-continued

| Wavelength, nm | $E_{1\ mg/ml,\ 1\ cm\ (H_2O,\ 20°\ C.)} \pm 6\%$ |
| --- | --- |
| 500 | 0 |
| 550 | 0 |
| 600 | 0 |
| 700 | 0 |
| 800 | 0 |
| 850 | 0 |
| 900 | 0 |
| 1000 | 0 |
| $E_{280}/E_{260}$ | 1,26 | it absorbs reversible in structure and biological activity on anion- and cation-exchangers, calcium phosphate gel, and hydroxyapatite and can be subjected in native form to volume-partition chromatography.

The invention further relates to a process for production and isolation of the above mentioned leukocytosis-inducing protein, which process is characterized in that mammalian serum is subjected to regulated and limited proteolysis by contact activation, the protein is then separated from other foreign constituents and proteins of serum in form of a crude serum protein concentrate fraction, and/or the protein is separated from other serum proteins by chromatography on hydroxyapatite, thus yielding the leukorecruitin.

A further subject matter of the invention are pharmaceutical compositions for specific influence on the defense state of mammalian organisms and for corrections of anomalies of leukocyte concentration in blood, which are characterized by a content of the above mentioned leukocytosis-inducing protein (leukorecruitin) or by a content of anti-leukorecruitin antibody serum and its fractions.

The leukocytosis-inducing protein of the invention is substantially free of biological side effects. Therefore it can further be characterized by the absence of many biological effects. For example it does substantially not show:
 increase of capillary permeability in the skin;
 spasmogenic activity on smooth muscles;
 spasmogenic activity on striated muscles;
 significant endotoxin content or effects in animals and humans identical with or similar to those of endotoxins;
 chemo-attraction (chemotaxis) of leukocytes in vitro;
 positive or negative chemokinetic activity on leukocytes in vitro;
 phagocytosis-stimulating activity on leukocytes in vitro;
 apparent shock or other detrimental (cardiovascular and cardiorespiratory) systemic effects of immediate or protracted type in animals and humans in vivo;
 pyrogenic activity in animals and humans in vivo;
 lysis effects alone or in the presence of plasma or serum on erythrocytes, thrombocytes, and leukocytes in vitro;
 phlogistic action in situ at reaction sites of formation or application of leukorecruitin;
 blood clot-inducing activity alone or in presence of plasma;
 aggregation of erythrocytes, thrombocytes and leukocytes alone, in salt solutions or in presence of plasma;
 mitogenic activity on leukocytes (spleen, blood or bone marrow);

mitogenic activity on endothelial cells of arterial vessels in vivo and in vitro;

induction of vascularization of tissue (cornea) by chemotropism;

chalone activity on leukocytes (spleen and bone marrow);

chalone activity on endothelial cells of arterial vessels;

The leukocytosis-inducing protein of the invention is produced as a humoral mediator by regulated, limited proteolysis through contact reactions of the blood, blood plasma, or blood serum, also in cell-free in-vitro systems. It represents normally no free and independent blood, blood-plasma, or blood-serum constituent. Its positive biological activity (leukocytosis reaction) is completely inhibitable by specific anti-leukorecruitin antibody serum fractions (anti-leukorecruitin immunoglobulins).

The blood, blood plasma, or blood serum in the blood circulation system is not necessary for positive action concerning the leukocytosis reaction: leukocytosis is also induced in culture fluids and protein- and cell-compatible blood substitutes. The threshold dose of the activity is 8 to 25 ng (1 to 3 pmol) of leukorecruitin/kg mammal. The active threshold blood concentration in vivo is about 30 pmol leukorecruitin/liter. Its $LD_{50}$ cannot be determined since lethal effects are not detectable even up to more than 100,000 fold dose of the physiologically active threshold dose.

The recruited leukocytes (leukocytosis) consist of a mixed white blood cell population with granulocytes as main component (granulkocytosis) and preference for mononuclear cells in the later phase (monocytosis). Beside mature cell elements, juvenile granulocyte forms ("bands") in particular are also recruited from the bone marrow into blood circulation.

The phase sequences of the leukocytosis reaction in vivo depend on the concentration (ED-dependent). The time shift of the amplitude (leukocyte number) and frequency (single, two-fold, or multiple) of phases in the leukocyte recruitment from the bone marrow as a function of the leukorecruitin dose is as presented in FIGS. 3 to 5.

DETAILED DESCRIPTION OF THE INVENTION

Leukorecruitin (for briefness referred to as "LR") is an inflammatory mediator with topobiochemically and biochemically specific action directed towards target cells (bone marrow) remote to the site of tissue injury and inflammation. Its biological function carried to its target (bone marrow) by the blood circulation is the recruitment of bone marrow leukocytes into the blood circulation (leukocytosis reaction). Leukorecruitin is not a normally present, independent blood or serum constituent. It is produced by regulated and limited proteolysis, e.g. through contact activation reactions which also activates the serum complement system. By these processes, leukorecruitin is formed concomitantly or sequentially in addition to a variety of other mediators from which only some of them are known, such as anaphylatoxin and cocytotaxin; cf. J. H. Wissler, Eur. J. Immunol., vol. 2 (1972), pp. 73 to 96.

Anaphylatoxin exerts a spasmogenic activity on smooth muscles. It acts on papillary muscles, and increases the capillary permeability of the blood vessels. Its shock activity is based on these effects. Furthermore, this protein is chemotactically active on eosinophil leukocytes. At physiological concentrations it has no significant chemotactic activity on neutrophil and mononuclear leukocytes. Moreover, it has no pyrogenic, leukocyte-aggregating and leukocyte-recruiting action. Cocytotaxin, which is physicochemically very similar to anaphylatoxin, only has a significant chemotactic activity on eosinophil leukocytes. In contrast to anaphylatoxin, it has no shock activity, no significant spasmogenic activity on smooth muscles, and no capillary permeability-increasing action. Like anaphylatoxin, cocytotaxin has no chemotactic activity on neutrophil and mononuclear leukocytes and no pyrogenic leukocyte-aggregating, or leukocyte-recruiting action.

Leukorecruitin (LR), isolated for the first time in highly purified, molecularly homogeneous, and crystalline form and characterized in accordance with the invention, is physicochemically very similar to anaphylatoxin and cocytotaxin. However, it has none of the activities of the latter two proteins. Thus, neither does it have chemotactic activity on either type of leukocytes and does not induce shock or other apparent systematically detrimental reactions, nor does it have chemokinetic or phagocytosis-stimulating activity for the various types of leukocytes, nor does it have clotpromoting or lysis activity on blood plasma and blood cells. Moreover, it does not increase capillary permeability, has no pyrogenic or spasmogenic action and does not affect proliferation of leukocytes or endothelial cells, neither by promotion (mitogen activity) nor inhibition (chalone activity).

In summary, LR acts specifically as regulator of the barrier between blood circulation and bone marrow (primary) storage pools of mature and juvenile leukocytes. Thus, it participates in homeostatic regulatory mechanisms of hematopiesis without displaying phologistic side-effects (e.g. pyrogen activity, etc.). For display of its biologically specific function, leukorecruitin has to enter circulation at the site of its formation (tissue injury, degeneration and inflammation). Then, it has to be carried by blood circulation to its target cells, the bone marrow as primary storage pools of juvenile and mature leukocytes. In these molecular properties, leukorecruitin is identical to typical proteohormones of classical endocrine glands (e.g. insulin and glucagon from pancreas cells). So far only autocrine and paracrine functions of sites of tissue injury, degeneration and inflammation have been clearly demonstrated. Hence, for the first time, sites of tissue injury, degeneration and inflammation are demonstrated to represent "mobile" endocrine glands as sources of a proteohormone like leukorecruitin which participates with one specific function in homeostasis principles of the body's defense system.

The LR protein differs from structural and functional properties of bacterial endotoxins in many of its biological and chemical features. To mention few of numerous differences: First, LR is an inflammatory mediator protein, whereas endotoxins have other structural features (lipopolysaccharides). Secondly, LR has no local phlogistic action on the site at which the inflammation occurs, whereas endotoxins have numerous of such activities (e.g. B-cell mitogen, indirect chemotactic activity for different types of leukocytes etc.). Similarly to the known hormones from endocrine glands, LR acts directly and specifically (e.g. without fever) only on target cells remote from the site of the inflammation (the barrier between bone marrow leukocytes and blood circulation, whereas the biologically unspecific endotoxins exert their effects on hematopoiesis indirectly and concomitant to fever reactions. It induces a leukocytosis reaction by recruiting new bone marrow leukocytes into blood circulation in vivo and into culture solutions in vitro in absence of serum complement system and without transient leukopenia reaction. The complex phase patterns of leukocytosis reactions induced by different LR doses is similar to the processes of leukocyte recruitment from the bone marrow obtained by antiserum inhibition experiments as described by K. Rother, op. cit. (1972) and by K. Rother et al. op. cit. (1978). In its further molecular properties, LR contrasts to endotoxins: Especially the far lower levels of it required in the blood for its direct activity (pmol/1) also indicates the similarity of this inflammatory mediator to hormones: they are comparable with the effective blood insulin or glucagon concentrations. The active threshold dose is 8 to 25 ng (1 to 3 pmol) LR per kg of organism. This corresponds to a calculated concentration of 30 pmol LR/liter blood. If these data are applied to in vivo conditions, this means that conversion of not more than 200 nl of blood serum protein solution per kg of the organism into leukorecruitin by limited and regulated proteolysis is sufficient to double the leukocyte count in the blood. In these molecular properties, in particular the pronounced biological specificity, the content of aromatic amino acids (tyrosine) and its 300- to 1000- times better specific activity, the LR protein obtained according to this invention by naturally regulated and limited proteolysis of mammalian serum through contact activation processes differs from other leukocytosis-inducing materials described in the literature; cf. K. Rother, op. cit. (1972) and B. Ghebrehiwet and H. J. Müller-Eberhard, op. cit. (1979).

LR can be determined quantitatively by physico-chemical methods with the aid of specific anti-leukorecruitin antibody serum prepared in accordance wtih the invention with molecularly homogeneous LR, or with the aid of its antileukorecruitin immunoglobulin fractions, by using the various conventional immunochemical methods (e.g. immunodiffusion, immunoelectrophoresis, radioimmunoassay or its enzymelinked variants). The activity of LR can be demonstrated in vitro by Rother's rat femur test, op. cit. (1972) and also in vivo. Intravenous administration of LR to guinea-pigs in the low dose of about 25 ng/kg (3 pmol/kg—calculated blood concentration about 30 pmol/1) causes at least doubling the leukocyte count of blood within 60 minutes. The increase of the leukocyte count and the frequency of its phases depends on the LR concentration.

FIGS. 3 to 5 show examples of the leukocytosis reactions provoked by various LR concentrations. The induction of the leukocytosis reaction in guinea-pigs after administration of LR is shown graphically. The figures show the leukocyte counts in the blood at varying times (the time of administration of the LR is taken as zero). FIG. 3 represents the leukocytosis reaction induced after administration of 100 ng (12.5 pmol), FIG. 4 the course induced after administration of 500 ng (60 pmol), and FIG. 5 the course induced after administration of 500 $\mu$g (60 nmol) of porcine serum LR/kg guinea-pig. The measurements were taken at intervals of about 3 to 30 min by counting the leukocytes present in a certain volume of blood (10 nl).

The leukocytosis can persist for 3 to 5 h, mono-, bi-, or even multi-phase reactions being possible. Juvenile granulocytic leukocyte forms (bands) can be recruited in addition to mature neutrophil (segmented) and mononuclear cells. Up to the non-physiological concentration of 100 $\mu$mol/1, LR has neither chemotactic, chemokinetic, nor phagocytosis-stimulating activity on neutrophil, eosinophil, and mononuclear humn, rabbit, porcine, canine, guinea pig, nor rat leukocytes, nor lytic and aggregating effects on blood cells, nor spasmogenic activity on smooth muscles of the guinea-pig ileum and coronaries, nor increasing activity on capillary permeability of the skin on guinea-pigs and rabbits when Evan's Blue is used as an intravenously injected dye marker. No mitrogenic activity on leukocytes and endothelial cells, or inhibition of cell mitosis can be observed even at high doses of LR. Finally, it has no shock activity, even after intravenous administration of 10,000 to 100,000-times the biologically effective dose in guinea-pigs or rabbits, no pyrogen action in rabbits [standardized method in accordance with Europ. Arzneibuch. (Europ. Pharmacopeia) vol. 2 (1975) pp. 56–59 and Brit. Pharmacopeia (1973) p.A 115, Appendix XIV I and U.S. Pharmacopoeia (1975) 19th revision, p. 613 (U.S. Pharmacopeial Convention, Rockville, Maryland) by rectal temperature measurement prior and after intravenous administration of LR), nor any other detectable systemic biological action so far assayed and described after its intravenous administration in the high dose of 1 mg/kg (about 100 nmol/kg) to guinea-pigs, rabbits and rats.

Figure 2B:
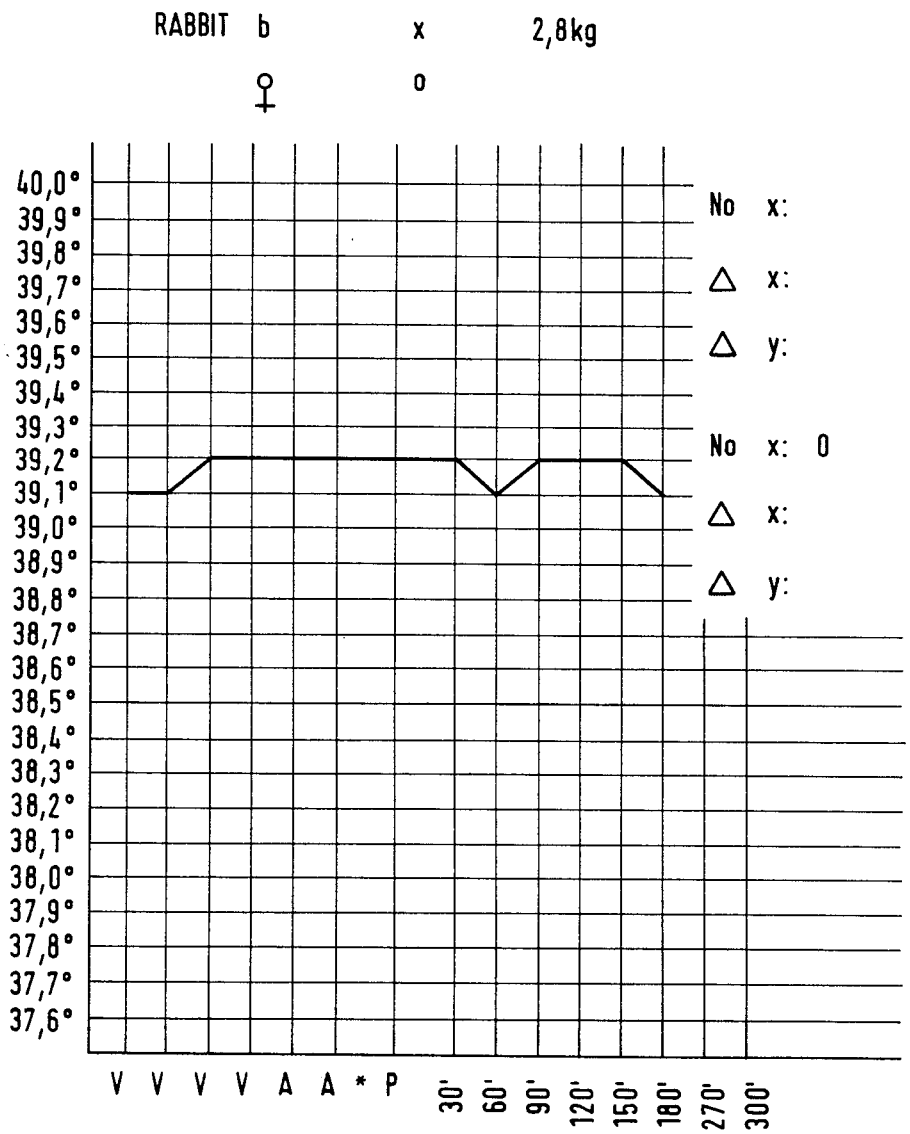
Figure 10:
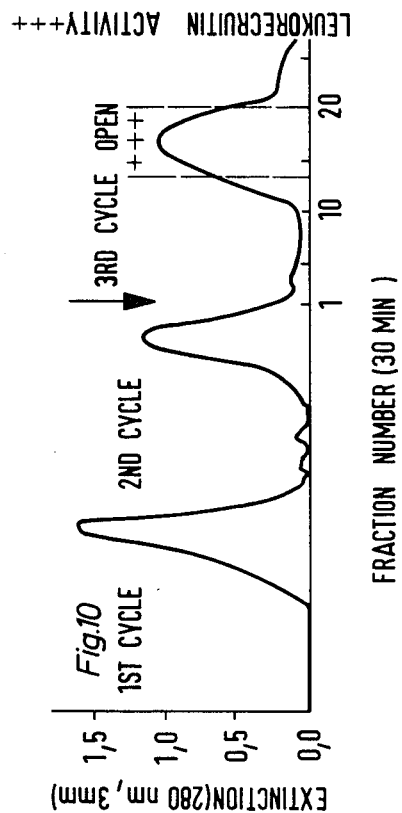
FIG. 10 graphically illustrates the further purification of the materials of this invention involving chromatography recovered from the operation graphically illustrated in FIG. 9.

FIG. 2 shows a standard pyrogen test performed in accordance with the 1975 edition of European Pharmacopoeia, carried out on three different rabbits (a, b and c) with an average weight of about 3 kg. Intravenous administration of porcine LR in a quantity of 1 $\mu$l (15 $\mu$g per animal $\overset{\triangle}{=}$ a total of 45 $\mu$g/8.5 kg animal $\overset{\triangle}{=}$ 0.63 nmol/kg) in 1 ml of (0.9 w/v-%) physiological saline shows no effect. This represents about 200 to 500 times the biologically active (leukocyte-recruiting) threshold dose. The diagrams in FIG. 2 are graphs of the course of the rectal temperature in the rabbits before (A), during (*), shortly after (P) and in addition 30 to 180 min after application. Only in rabbit (a) a rise in temperature of 0.1° C. can be observed. The same negative result in terms of febrile activity of porcine LR has been obtained in normal healthy humans, in which LR induces a strong leukocytosis reaction but displays no apparent other side effects; cf. St. E. G. Burdach, K. -G. Evers and J. H. Wissler, "Leukorecruitin in der Diagnostik des Morbus Kostmann (Infantile genetische Agranulocytose)", Commun. 77th Meeting Deutsche Gesellschaft Kinderheilkunde, No. 303, Düsseldorf Germany, September 1981. This supports the idea that highly purified, defined inflammatory mediators and hormones are valuable "drugs" of specific action and being far superior to synthetic drugs which show numerous side-effects; cf. St. E. G. Burdach, K. -G. Evers and J. H. Wissler, Z. Immun. -Forschung-Immunobiology 159 (1981). The 1975 European Pharmacopeia edition, the British (1973) and American (U.S.P.) (1975) standards, allow the designation "pyrogen-free" to be applied to preparations for which the sum of the fluctuations of the rectal temperature in a total of three experimental rabbits does not exceed the value of 2.65° C. and especially is below 1.15° C. According to these definitions, the LR preparation of this invention is pyrogen-free and is devoid of febrile activity. This extremely sensitive criterion for contamination of proteins with bacterial endotoxins and other ubiquitous pyrogens demonstrates the great efficacy of the process of the purification of LR and is an obvious parameter for biological specificity.

The LR prepared and obtained according to the invention is a valuable, endogenous and active principle that can be used to act specifically on the defense state of the body, e.g. the immune status. LR is useful for specifically influencing leukocytosis reactions and leukocyte functions, for example inflammatory reactions and in cardiac infarction. In addition, the LR can be used to prepare leukorecruitin antibodies for specifically influencing the course of leukemia. Further applications emerge from so far established clinical investigations on LR for specificalluy influencing distinct leukopenia states; e.g. for differential diagnosis of infantile genetic agranulocytosis from pseudoneutropenia states and for determination of mobiliziable leukocyte reserve in the bone marrow, as well as for possible therapeutic use in individuals bearing granulocytopenia following endotoxinemia and bacterial infections with otherwise fatal prognosis in which classical therapy with cortisone is problematic due to its suppressive effect on T-lymphocytes and monocytes; cf. St. E. G. Burdach et al. op. cit. (1981).

The results of these clincal investigations demonstrate that highly purified, anaphylatoxin- and encotoxin-free, serum-derived LR is active in healthy humans and acts specifically in terms of the biological (transient leukocytosis) reaction induced; but, as other mediators and hormones, it is not species-specific. No other significant persistant, immediate or protracted systemic or local reactions in terms of hematological criteria, cardiorespiratory functions, body temperature, conscious behavior and need of intensive care preparations so far could be monitored Like hormones of animal tissue oriogin (e.g. porcine or bovine insulin), porcine serum-derived LR can be used in humans for specific purposes. In contrast to normal healthy humans, in individual bearing infantile genetic agranulocytosis which is characterized by a congential neutropenia by arrest of cell multiplication and maturation between myeloblast and metamyelocte stages and void marrow storage pools for mature leukocytes, LR cannot correct low blood leukocyte levels to normal. Hence, in humans, LR may represent suitable tool to differentiate this disease from other leukopenia states; as in animals, LR acts also in humans mechanistically specific (blood circulation—marrow barrier) in leukopoieses and does not effect the proliferation pool of leukocytes in the bone marrow.

For those purposes, the LR is adminstrated parenterally and preferably intravenously in formal pharmacological form to mammals, e.g. humans in a daily dose of 10 ng/kg to 100 μg/kg); cf. St. E. G. Burdach el al., op. cit. (1981).

Another subject matter of the invention is a procoess for the biotechnical preparation and isolation of LR. It is characterized in that blood, plasma or serum as starting materials are subjected to a maturally regulated and limited proteolysis through contact activation, which can be performed within a short time by using newly invented forms of contact-substances. The proteins of the contact-activated serum are then separated from other serum constituents and chromatographed to yield the LR protein. By this procedure an already highly enriched and relatively pure leukorecruitin preparation is thus obtained, which subseqeuntly can be separated from residual accompanying foreign proteins by further steps of purification.

After this final purification a molecularly homogeneous, highly purified and crystalline (crystallizable) LR is obtained. It is free of phthalate derivatives as plasticizers dissolved from plastic vessels and occurring in animal food as food expanders and it is free of dichlorobenzoic acid derivatives derived from chemical food pollution. Both groups of substances occur in animal blood as trace components. They can be isolated separately and are identified by gas-chromatographical and mass spectrometic analysis.

In the process in accordance with the invention, following the contact activation of the serum in which the LR is produced, a LR-containing crude serum protein concentrate fraction is separated from the other serum constituents. This can be done favourably by a cation exchange reaction for which CM-Sephadex C 50 is preferred as the cation-exchanger. For isolation of LR the LR-containing positively adsorbed and eluted protein material thus obtained which is separated from other, negatively adsorbed serum constituents (e.g. also lipids, glycoproteins, etc.), can be chromatographed on hydroxyapatite. However, for reasons explained afterwards, in the process in accordance with the invention it is preferred to separate at least a part, and in particular a major fraction of accompanying foreign (inactive) proteins from the LR-containing crude serum protein concentrate fraction by distinct separation processes before chromatography on hydroxyapatite. The mediators which are present in the crude serum protein concentrate fraction and of which LR is one representative, are trace substances occurring in contact-activated serum only in very small quantities. 100 liters of contact-activated serum (corresponding to 250 to 300 liters of blood) contain about 7 to 8 kg of protein in addition to other subtances, of which only about 0.3 to 3 g (depending on the species and the type of the contact reaction) are represented by LR. Of this amount of LR, a maximum of 10 to 20% can be isolated, since purification processes are complex and have only a limited yield. However, a prerequisite for the practical utilizatiom of LR is its preparation and isolation in appreciable (mg-) quantities. For this purpose very large volumes of blood have to be handled. In principle, whole fresh blood or blood plasma can also be used as a starting material and submitted to contact activation. However, since neither the blood cells in the whole blood nor the fibrinogen in the blood plasma are necessary for the formation of LR as a humoral mediator, it is easier and preferable to use fresh blood serum as starting material. Since the proteins participating in contact activation processes of blood serum are very labile and degenerate time-dependently on out-dating, fresh serum prepared from fresh blood by coagulation is submitted (within 24 h) to the contact-activation process for efficient production of LR.

The use of hydroxyapatite is of essential significance for the structure-conserving isolation of pure LR. However, in general, for technical and economic reasons, considerable difficulties arise from chromatography of larger volumes of solutions of high protein concentrations on hydroxyapatite columns, e.g. for chromatography of large quantities of the crude serum protein concentrate fraction. On the one hand, larger protein amounts tend to support the strong tendency of hydroxyapatite to block up, thus becoming unusable as stationary matrix in chromatography. On the other hand, hydoxyapatite is very expensive. Its use on larger scales is not economical. For these reasons, in the process in accordance with the invention, separation of a large part of the accompanying foreign proteins by appropriate biotechnical purification steps from the LR-containing serum protein concentrate fraction for reduction of the volume of concentrated protein solution is preferred prior to its chromatography on hydroxyapatite.

In general, purification processes for the proteins and other natural substances comprise sequences of combined separation techniques. Subtle differences in molecular size, charge, form, structure, stability, and nature of the molecular surface between the desired natural substance and the accompanying inactive foreign materials are used in such purification steps for their separation. Accordingly, a large number of combinations of various modifications of separation techniques can be devised for purification of a protein. The nature and the conditions of separation steps used, but as well their sequential combination, are of paramount significance for operational properties, technical practicability, optional automatisation possibility, and economics of a purification process and also for yield and molecular quality of a natural product investigated. Particular attention has to be focused on optimum form of separation steps and on their ingenious combination into a purification sequence within a frame of structural and functional stability and other molecular parameters of the substance under investigation. This implies that use of identical or similar separation principles (e.g. molecular sieve filtration, dialysis, ion-exchange adsorption, etc), but in a different combination, can be of a decisive and paramount importance for practice and economics of a purification process as well as yield and quality of the product obtained. In some cases, use or omission of a single technique (e.g. hydroxyapatite chromatography, zone-precipitation chromatography, etc.) at a distinct position in the purification sequence, or within a partial sequence, is of decisive significance for yield and quality of the desired natural product as well as for practice and economics of the purification process. These general ralationships and basic principles inherent to purification processes of natural products are clearly illustrated e.g. by some well known facts. Thus, within an economically and technically operable process for the purification of a natural product, initial dialysis, ultrafiltration or lyophilization steps are not recommended prior to reduction of initial volumes through removal of foreign materials of the crude starting extract (e.g. blood or serum) by a factor of at least 500–1000 through other techniques.

In a preferred embodiment of the process in accordance with the invention a part of the accompanying foreign proteins is separated from the LR-containing crude serum protein concentrate fraction or contact-activated serum by positive adsorption on calcium phosphate gel or by negative adsoption on an anion-exchanger, particularly DEAE-Sephadex-A 50 on which LR can be negatively or positively adsorbed respectively. In these embodiments, prior to chromatography on hydroxyapatite the first technique achieves reduction of about 10%, and the second method of about 30% of the amount of the foreign proteins. On the one hand, this reduction of the volume of the concentrated protein fraction is relatively small. On the other hand, the processes can be performed quickly and simply. Thus, the embodiments are particularly useful for work on the laboratory or semi-industrial scales. Together with the preparation of the crude serum protein concentrate fraction by cation exchange, a volume reduction from 1000 ml serum to about 25 ml protein solution can be achieved prior to application of the protein mixture onto the hyroxyapatite column. A useful embodiment of particular preference is that the LR-containing serum proteins first are submitted to an anion exchange step and then to a calcium phosphate adsorption step.

In a further and particularly preferred embodiment removal of a large part of the accompanying foreign proteins from the LR-containing serum protein concentrate fraction or serum is performed by fractional elution of reversibly salted-out protein precipitates and/or precipitation with a water-soluble alcohol and/or at least one molecular sieve filtration. A variant procedure particularly preferred in this embodiment comprises at least two of the said separation steps in sequence.

The biotechnical processes in accordance with the invention allow processing of large amounts of blood, plasma and serum and thus fast and economical isolation of appreciable quantities of LR. In accordance with the invention, the major part of the accompanying foreign inactive proteins is removed prior to chromatography on hydroxyapatite, which is a critical step for LR quality. Thus, only a small LR-containing fraction (in the preferred embodiments less than about 0.09% of starting serum volume) of the total amount of serum protein has to be applied to the hydroxyapatite column. A batch can be started for example at least with 100 to 200 liters of contact-activated serum (about 300 to 600 liters of blood). For example, starting with 100 liters of contact-activated serum, the protein solution volume obtained still containing almost all the LR can be thus reduced to less than about 100 to 200 ml, which represents a volume reduction factor of about 500–1000, prior to application onto the hydroxyapatite column. In addition, the process allows to isolate the investigated mediator in its native, biologically active conformation.

The process for biotechnical production of a LR-preparation and also of the molecularly homogeneous, crystalline LR protein in a biologicaly specific and active form will now be specifically explained in detail.

A. BIOTECHNICAL PREPARATION OF LR IN SERUM AND OF CONTACT REACTION AGENTS. REGULATED AND LIMITED PROTEOLYSIS OF THE BLOOD, PLASMA OR SERUM BY CONTACT ACTIVATION. SEPARATION OF THE LR-CONTAINING CRUDE SERUM PROTEIN CONCENTRATE FRACTION FROM THE OTHER SERUM CONSTITUENTS, AND PREPARATION OF LR-CONTAINING CRUDE SERUM PROTEIN CONCENTRATE FRACTION.

As already mentioned, mammalian blood, plasma or serum serves as starting material for the biotechnical preparation and isolation of LR in accordance with the process of the invention. Because of its easy availability, human, bovine, equine, porcine, ovine, canine, feline, rabbit, rat, or guinea-pig serum is preferred. The serum is obtained in the usual manner by coagulation of blood and separation of the clot, for example by filtration and/or centriguration. Then, it is incubated, preferably under continued stirring, for the generation of LR with a contact substance, e.g. with dextran, yeast, bacterial endotoxins, or with an immuno complex.

In accordance with the invention a specially prepared physical form of dextran or baker'yeast is preferably used for the LR generation. These specially prepared forms of the two contact substances allow outstanding short incubation periods for generation of LR from its precursors in blood, plasma or serum. Thus, with them, e.g., 1 h at 37° C. is sufficient, whereas other usual contact substances require an incubation time of up to 5 days; cf. G. Ghebrehiwet and J. H. Müller-Eberhard, op. cit. (1979). By contact activation of the blood, plasma, or serum various blood protein systems of complex compositons are activated. Among these sytems are the known coagulation, kinin and complement protein systems. In the activation process by contact with exogenous, high molecular substances, part of the LR-inactive proteins of these systems are converted into proteolytic enzymes. In turn, they cleave another part of proteins as components of these systems in a complex manner in form of a proteolytic activity cascade restricted by regulatory loops. LR and other already mentioned humoral inflammatory mediators are generated by this process. The physical form of a contact substance often decides whether or not and how fast and to which extent these enzyme activity cascades are triggered. For example, neither most of the low molecular nor the high-molecular readily soluble dextran forms can activate the cascade of the complement system at a suitable reaction rate. However, if such readily soluble dextran is converted into a different, particular physical form, it becomes capable of activating such serum protein cascades. This aim is fulfilled by the process in accordance with the invention.

All types of dextran with a molecular weight above 100,000 dalton are suitable as starting materials for the preparation of a contact reaction-active dextran. The readily soluble contact reacton-inactive dextran is heated in a dry air current for 7 days at 90° to 160° C. and preferably 110° to 130° C. After cooling, it is broken to a coarse form and then ground to a granular form with a mean particle size of 0.5 to 3 mm (e.g. in a bowl mill or a mortar). A contact reaction-active, granular, largely insoluble dextran form is obtained that can be swollen in water or serum to a gel. Upon contact with blood, plasma or serum over a period of 1 h between 20° and 45° C. LR is generated.

Prior to its use as a contact agent for LR formation, baker's yeast is boiled in up to 10-times its volume of water. The insoluble cellular particle mud is separated from the cellular components dissolved in the supernatant liquid by decantation or centrifugation (10,000×g for at least 5 min) and repeatedly boiled (at least four times) in water until the supernatant has an extinction of less than 0.1 at 280 and 260 mm. The insoluble, contact reaction-active cellular particle residue of the yeast is lyophilized, dried, or stored frozen in the wet state and used in a quantity on dry weight basis.

The contact activation of the serum of the LR generation is stopped by cooling and removal of the contact agent after a sufficient incubation period between 20° and 45° C., preferably at 37° C. This period is preferably for example about 1 h with dextran or baker's yeast. The incubated serum is preferably cooled to a temperature of about 0° to 8° C. All the following process steps are preferably performed within this temperature ranged unless otherwise specified. Similarly, in the following to all solutions preferably 0.001 mol/1 cysteine is added. The insoluble contact substance added for incubation is completely separated in a usual manner from the incubated supernatant contact-activated serum, for example by decantation, filtration, or centrifugation (10,000×g for at least 5 min).

For the preparation of an LR-containing crude serum protein concentrate fraction, the incubated LR-containing serum is treated with a cation exchanger to separate the majority of proteins from other serum constituents. Examples of cation exchange matrices suitable for this purpose are dextrans crosslinked with epichlorohydrin (Sephadex) carrying functional groups with cation exchange capacity. These can be readily regenerated after use and repeatedly processed. It is preferable to use a weakly acidic cation exchanger, such as CM Sephadex C-50-having $Na^+$ as mobile counterion, and to perform the treatment at a pH between 4 to 6. To facilitate the charge process and to approach more ideal equilibria conditions prior to treatment with the cation exchanger the contact-activated serum should be diluted with a protein-compatible salt solution having a maximum ionic strength equivalent to 0.2 mol NaCl/1. This salt solution can be used at the same time to adjust the pH. A special example of a salt solution for this purpose is a 0.001 mol/1 potassium phosphate-acetate buffer containing 0.2 mol/1 NaCl, 0.001 mol/1 cysteine and having a pH of 4.5. This cation-exchange reaction may be performed in terms of a chromatographic process or, technically easier, as a batch process.

The swollen cation exchanger is added to the serum in a sufficient quantity to absorb the main protein fraction of serum. As a rule, about 1 volume part of swollen ion exchanger per volume part of contact-activated serum is sufficient for this purpose. Then, the supernatant is separated from the cation exchanger charged with LR and other proteins, for example by decantation or centrifugation.

The charged cation exchanger is freed from adhering, negatively adsorbed serum components by washing with water or a salt solution, having a maximum ionic strength equivalent to 0.2 mol NaCl/l. Preferably a pH of about 4 to 6 and a maximum temperature of about 15° C. is used. A special example of a salt solution suitable for the washing-out process is the mentioned potassium phosphate-acetate buffer having a pH of 4.5.

The washed protein-charged cation exchanger is now eluted with a protein-compatible aqueous salt solution. A salt solution of high ionic strength with a pH of about 4 to 10 is preferably used for this purpose. Special examples for such salt solutions are aqueous 0.5 mol/l solutions of potassium phosphate of pH 6.5 to 7.5 or a 2 to 5 mol/l solution of sodium chloride of the same pH.

The eluate obtained containing the bulk of serum proteins and LR is now concentrated prior to subsequent separation of proteins. This concentration process which separates the bulk of aqueous salt solution from the proteins, can be done in various ways. For example, the majority of the proteins, including LR can be precipitated completely by adjusting the eluate to an ammonium sulfate concentration of about 3.25 to 3.7 mol/l (salting-out precipitation of proteins at 80–90% salt saturation). For this purpose, ammonium sulfate is added in a quantity of approximately 630 g/l eluate (saturation of about 90%). During this process, the pH is preferably kept between about 4 and 9. The precipitated, LR-containing protein mixture is separated from the almost protein-free supernatent, for example by filtration, decantation or centrifugation, and obtained as a protein mud.

Unless otherwise stated, centrifugation is preferably carried out at least at 10,000 ×g for a minimum of 45 min., and preferably for 1 h, in a one-step process. Or it can be carried out in two stages, at lower forces in the first stage for removal of the bulk of precipitated proteins; and then, for the supernatant of the first stage containing residual fine protein particles at higher forces, e.g. 20,000 to 50,000×g, by flow-through centrifugation.

The eluate of the cation exchange process can also be concentrated by using other methods, for example by lyophilization or ultrafiltration and dry dialysis, preferably against polyethylene glycol (molecular weight 20,000 dalton) at membranes with exclusion limits of preferably 500 to 1,000 dalton. But these processes are time-consuming and relatively expensive. In this case, for further performance in accordance with the process of the invention, however, the obtained protein concentrate must likewise be adjusted to an ammonium sulfate concentration of 3.7 mol/l which yields again the aforementioned protein mud.

In all cases the LR-containing protein precipitate formed (serum protein concentrate fraction) is obtained in form of a protein mud containing 90% ammonium sulfate salt saturation. For purpose of further purification of LR, this mud is used as such in the manner described below.

B. CRUDE PURIFICATION OF LR: SEPARATION OF THE BULK OF THE ACCOMPANYING FOREIGN PROTEINS OF LR. PREPARATION OF A "CRUDE LR PREPARATION"

In one embodiment of the process in accordance with the invention, part of the LR-accompanying foreign proteins and other substances (such as lipids) are separated by positive adsorption on calcium phosphate gel from LR in the LR-containing crude serum protein concentrate fraction obtained in stage A. For this purpose, the LR-containing crude serum protein concentrate fraction obtained in stage A is dissolved, for example, in 0.001 mol/l sodium-potassium phosphate buffer containing 0.2 mol/l NaCl, 0.001 mol/l crysteine and having a pH of 6.60. For salt removal, the LR-containing protein solution is subjected to dialysis or ultrafiltration against the above mentioned buffer at a membrane with an exclusion limit of 500 to 1,000 dalton. Or, for removal of ammonium sulfate, it is subjected to a desalting molecular sieve filtration chromatography with an appropriate exclusion limit (e.g. on Sephadex G10, G15 or G25) until it is salt-free. The ammonium sulfate-free protein solution equilibrated in the said buffer is treated with 50 ml of calcium phosphate gel per volume unit of crude serum protein concentrate fraction solution obtained from 1 l of serum. Treatment under stirring is carried out for about 1 hr. Then, the gel is separated off by centrifugation for 5 min at 10,000×g. The residue gel is washed three times with 100 ml portions of the said buffer. The washing buffer fractions are combined with the negatively adsorbed, LR-containing supernatant protein solution. The combined protein solution obtained can be concentrated in the described manner by salting-out precipitation of the proteins with ammonium sulfate or with one of the other mentioned methods. The precipitated, LR-containing protein mud obtained after concentration can then be further processed in one of the following manners.

In a second embodiment, a part of the LR-accompanying foreign proteins is separated from the LR by negative adsorption and/or elution chromatography on an anion-exchanger (e.g. DEAE-Sephadex A50), either directly contact-activated serum, or from the crude serum protein concentrate fraction obtained in Section A, or from a concentrated protein solution obtained by calcium phosphate gel treatment of the crude serum protein concentrate fraction. If contact-activated serum is used for the anion exchange step, 1 volume part of serum is mixed with at least 4 volume parts of water or of a protein-compatible salt solution for reduction of the NaCl concentration to maximum 0.03 mol/l. The mixture is adjusted to a maximum tris-HCl concentration of 0.01 mol/l, a cysteine concentration of 0,001 mol/l and a pH of at least 8.0. 2 volume parts of a swollen anion exchanger per volume part of serum is added. Examples of suitable anion exchangers are dextran matrices cross-linked with epichlorohydrin (Sephadex) carrying functional groups with anion exchanger capacity. These exchangers can be regenerated for repeated further use. It is preferable to use a weak anoin exchanger in the Cl$^-$form such as DEAE-Sephadex A-50, pre-swollen and equilibrated in a buffer. Performance of the treatment is preferred at a pH of 8 to 10. A special example of a buffer for this purpose is 0.01 mol/l tris-HCl containing 0.03 mol/l NaCl, 0.001 mol/l cysteine, and having a pH of 8.0.

The anion exchanger is added to the serum in a sufficient amount for complete adsorption of the LR and the other positively adsorbing accompanying proteins. The reaction can be carried out either as a chromatographic process or as an easy and fast batch adsorption technique. In the latter case, the supernatant liquid containing negatively adsorbing foreign proteins is separated from the anion exchanger which is charged with the positively adsorbing LR and other positively adsorbing proteins, e.g. by filtration in a Büchner funnel or in a chromatographic column, or by decantation or centrifugation. The charged anion exchanger is freed from adhering negatively adsorbing serum constituents by washing with water or a salt solution having a maximum ionic strength equivalent to 0.03 mol/l NaCl, preferably at a pH of 8 to 10.

The maximum preferred temperature is about 15° C. A special example of a salt solution suitable for the washing-out process is the said tris-HCl buffer of pH 8.0.

The anion exchanger on which LR and other proteins are adsorbed and which is freed from the negatively adsorbed serum constituents, is eluted with a protein-compatible aqueous salt solution, having an ionic strength higher than 0.1 mol/l NaCl and a pH between 6.0 an 10.0. A salt solution of high ionic strength and a pH between 4.0 and 10.0 is preferably used. A special example of such a salt solution is a 2.0 mol/l NaCl solution, buffered to pH 6.5 with 0.01 mol/l piperazine-HCl and containing 0.001 mol/l cysteine.

In the anion exchange reaction is carried out as a chromatographic process, elution of the LR and other positively adsorbed proteins can also be done by a linear NaCl concentration gradient. LR is eluted at an ionic strength of 0.15 mol/l NaCl buffered to pH 6.5, preferably e.g. by the mentioned piperazine-HCl buffer.

The LR-containing protein eluate is then concentrated for subsequent further separation of the proteins in the usual manners, preferably by salting-out precipitation of the proteins at an ammonium sulfate saturation of 90%. The concentrated LR-containing protein precipitate mud obtained is further purified according to one of the following preferred techniques.

Otherwise, the anion exchange reaction can be preferably performed in sequence after calcium phosphate gel treatment of the crude serum protein concentrate fraction (obtained according to the Section A) or directly with the latter fraction without calcium phosphate gel treatment. For these purposes, the concentrated precipitate muds are first dissolved in a minimum volume of protein-compatible liquid. For complete removal of ammonium sulfate, the solutions obtained are then subjected to dialysis at a membrane with an exclusion limit of 500 to 1,000 dalton against water or protein-compatible salt solution of low ionic strength, preferably against the said 0.01 mol/l tris-HCl buffer containing 0.03 mol/l NaCl, 0.001 mol/l cysteine and having a pH of 8.0. The clear protein solutions are treated in exactly the same way for the anion exchange reaction as described for the contact-activated serum.

According to the third and particularly preferred embodiment of the process in accordance with the invention, the separation of foreign proteins from the LR-containing crude serum protein concentrate fraction obtained in Stage A is carried out by fractional elution of salted-out protein precipitate and/or precipitation with a water-soluble alcohol and/or at least one molecular sieve filtration.

It is possible to remove a considerable amount of LR-accompanying foreign proteins by only one performance of one of these purification methods in accordance with the invention. Thus, a satisfactory volume reduction of the crude serum protein concentrate fraction is achieved prior to charge of the hydroxyapatite column. For example, in the physiological pH range about 30% of the accompanying foreign proteins can be removed by fractional elution, about 60 to 70% by precipitation with a water-soluble alcohol, and up to 90% by molecular sieve filtration. However, as a general property of polyelectrolytes, proteins of the crude serum protein concentrate fraction tend to adhere very strongly together. Furthermore, no ideal equilibria and distributions are obtained with concentrated macromolecular polyelectrolytes solutions as represented by proteins. Therefore, for example, in spite of different molecular weights of proteins, by molecular sieve filtration, no complete (ideal) separation according to their molecular weight proper is obtained at once. Hence, it is necessary to perform at least two of the said separation processes in sequence. Thus, preferably the crude serum protein concentrate fraction is, for example, first fractionally eluted and then subjected to a molecular sieve filtration. Or, the LR-accompanying foreign proteins are first precipitated with a water-soluble alcohol, and, then, a molecular sieve filtration is carried out. Moreover, combinations of fractional elution and/or precipitation with a water-soluble alcohol with at least one preparative and one analytical molecular sieve filtration are preferred. All these combinations of the mentioned separation steps constitute objects of the invention. It is evident that certain sequences of separation steps are of less advantage than other combinations. Thus, for example, it is imperative to perform a preparative molecular sieve filtration before an analytical molecular sieve filtration: In reverse order of performance, difficulties in handling, economics and yield are obvious.

Particularly preferred embodiments of the process in accordance with the invention for removal of a large fraction of LR-accompanying foreign proteins consist of the following combinations of separation techniques:
(a) a fractional elution step followed by two preparative and then one analytical molecular sieve filtration;
(b) a fractional elution step followed by one protein precipitation step with a water-soluble alcohol, then followed by one preparative, and lastly by one analytical molecular sieve filtration;
(c) a protein precipitation step with a water-soluble alcohol followed by one or two preparative and lastly by one analytical molecular sieve filtration.

One of the numerous outstanding advantages of any sequential combination of these different techniques is due to the fact, that, in principle, no intermediary dialysis or ultrafiltration step must be used for removal of salts, since these steps are not sensitive to unwanted salts.

The performance of the individual separation processes for the separation of the bulk of the accompanying foreign proteins from the LR contained in the crude serum protein concentrate fraction in accordance with the process of the invention will now be described in specific detail.

Fractional elution of the protein precipitate of the crude serum protein concentrate fraction separates proteins largely independent of their molecular weight. The part of the LR-accompanying foreign proteins that is soluble at higher ammonium sulfate concentrations than LR, is separated from the concentrate. This separation method, therefore, is performed in the form of a batch process in the concurrence with the preparation of the serum protein concentrate fraction. It has the advantage of being rapid and unlimited in capacity. If serveral separation steps are used in sequence, the fractional elution is, therefore, preferably carried out first.

Prior to fractional elution, the protein mixture to be treated must be adjusted to an ammonium sulfate concentration sufficient for the precipitation of all the proteins. Such a suspension has ammonium sulfate content of about 3.7 mol/l (at 0° to 80° C.); i.e. it is saturated to the extent of 90%. Adjustment to this ammonium sulfate content is done, for example as described (Section A), after separation of the entire LR-containing serum protein eluate from the cation exchanger.

Concentration of proteins in the cation exchanger eluate is carried out either directly by salting-out precipitation of proteins with ammonium sulfate. Or, if the eluate had been concentrated by a different process, such as ultra-filtration, dry dialysis or lyophilization, ammonium sulfate is added to the concentrate to result the given saturation.

For the fractional elution of proteins, ammonium sulfate concentration of the crude serum protein concentrate fraction is adjusted to about 2.6 mol/l by addition of a protein-compatible liquid. Water or, preferably, a buffered salt solution can be used as such a liquid. Preferably, a pH between 4 to 8.5 and a temperature of approximately 0° to 8° C. is maintained. A special example of a suitable salt solution is a 0.001 mol/l sodium-potassium phosphate buffer containing 0.1 mol/l NaCl and having a pH of 6.3. When such an (ammonium sulfate-free) salt solution of water is used, about 0.4 volume parts per volume part of the crude serum protein concentrate fraction (as protein mud) is necessary to achieve the desired reduction in the ammonium sulfate concentration.

The ammonium sulfate concentration of the obtained protein suspension shall not be much lower than about 2.6 mol/l. Otherwise the LR is dissolved as well. On the other hand, adjustment to an ammonium sulfate concentration much higher than about 2.6 mol/l is not advantageous, because less foreign proteins would be dissolved.

Thus, decreased efficiency of the fractional elution would result. To obtain a favorable solution equilibrium at the given ammonium sulfate concentration, the protein suspension is maintained at the given temperature and pH conditions for some time, preferably about 10 to 24 h with stirring. The remaining protein precipitate is then separated from the supernatant, for example by decantation or centrifugation.

In principal fractional elution is the reverse process of fractional precipitation. Therefore, this purification step, may be carried out as fractional precipitation as well. In such a case, however, the eluate of the cation exchange process is adjusted to an ammonium sulfate concentration of only about 2.6 mol/l instead of about 3.7 mol/l. The precipitating LR-containing protein fraction is separated from the soluble supernatant protein solution. However, as is known from principles in protein fractionation, due to kinetics of formation of solubility equilibria, fractional elution may have selective advantage over fractional precipitation as separation process. It may give higher yields than fractional precipitation. This also applies to this LR fractionation process.

Separation of a part of LR-accompanying foreign proteins from LR by protein precipitation with a water-soluble alcohol takes advantage from the fact that, under certain conditions, a fraction of foreign proteins, but not LR, is precipitated upon addition of a water-soluble alcohol to the protein solution. As for a rotational elution, this protein precipitation with alcohol is largely independent of the molecular weight of proteins. A large part of the LR-accompanying proteins is separated from LR. This separation step is preferably performed after the fractional elution process or instead of the latter purification step. In this way, for the following molecular sieve filtration the charge of the column used is considerably reduced.

Treatment with alcohol is carried out at a pH of about 3.5 to 5.5 and preferably at about 4.0, and at a maximum temperature of 8° C., and preferably between 0° to 5° C. Maintenance of given pH range is crucial. At lower pH, isolated proteins may be damaged. Higher pH may lower efficiency of the precipitation step. However, adjusting the pH only to the given range without addition of alcohol does not bring about precipitation of the foreign proteins.

The water-soluble alcohol is added in amounts of about 180 to 250, and preferably about 200 volume parts per 1000 volume parts of the protein solution. Smaller quantities of alcohol do not achieve complete precipitation. Higher alcohol concentrations result in no better precipitating effects. They may, however, increase the risk for damage of the mediator protein investigated by altering its conformation. Special examples of suitable water-soluble alcohols are methanol, ethanol, propanol, and ethylene glycol. Ethanol is preferred as the water-soluble alcohol.

Protein precipitation with alcohol is performed with the (ammonium sulfate-containing) muddy crude serum protein concentrate fraction obtained from the eluate of cation exchange process (Section A) or with the muddy protein residue obtained by the fractional elution step after their solution in a minimum volume of a protein-compatible liquid. A special example of a suitable solution is 0.01 mol/l ammonium acetate solution containing 0.2 mol/l NaCl and having a pH of 5.0. The pH of the solution is then adjusted to the given range; for example with glacial acetic acid after each the alcohol is added.

For precipitation of foreign proteins, the solution is then maintained under the given conditions for some time, preferably with stirring. The precipitated foreign proteins are then separated from the supernatant which contains LR dissolved, for example by decantation or centrifugation. The alcohol can be removed from the LR-containing protein solution, for example by dialysis, ultrafiltration, or lyophilization. If a molecular sieve filtration step follows for further purification of LR, the alcohol (46 dalton for $C_2H_5OH$) may be directly separated from the LR (8.500 dalton) without the above mentioned auxiliary methods.

Molecular sieve filtration achieves separation of proteins according to their molecular weights. Since the bulk of the foreign proteins have molecular weights higher than LR, they can be separated off in this manner. A hydrophilic water-swelling molecular sieve as matrix is used for separation of the proteins by molecular weight. Examples of suitable molecular sieves are dextrans cross-linked with epichlorohydrin (Sephadex), agaroses cross-linked with acrylamide (Ultrogels), and three-dimensionally cross-linked acrylamides (Biogels), the exclusion limits of which are higher than the separation limits used. Sephadex G50 types of molecular sieves are preferably used for the purpose of LR isolation.

If several separation steps are used, the molecular sieve filtration is preferably carried out after fractional elution and/or protein precipitation with a water-soluble alcohol. In this way, a major fraction of foreign proteins from all molecular weight ranges is already removed by the preceding separation steps. The proteins mass to be removed by the molecular sieve step is thus already considerably smaller. Depending on length-to-diameter ratio of the column used and/or particle diameter of the gel matrix, molecular sieve filtration is termed "preparative" or "analytical". A molecular sieve filtration is preparative when the chromatography is performed on columns with a length-to-diameter ratio of up to 10:1 and a charge of the column of up to ⅓ of its capacity in terms of total separation volume of the matrix. Analytical molecular sieve filtration means a length-to-diameter ratio larger than 10:1, and preferably about 50:1, and a maximum charge of the column of up to 3% of its capacity.

In preparative molecular sieve chromatography, gel matrices with the largest possible particle size are used for maximum flow-through rates of mostly viscous protein solutions applied at reasonably low pressures. In analytical molecular sieve filtration the particle size ranges of the gel matrix are selected as small as possible, to obtain a maximum number of theoretical plates, a flow rate of the mobile phase in the range of 2 to 4 cm/h combined with a pressure which is limited to technical and safety aspects. These parameters are dependent on the structure of the gel matrix and may vary from gel to gel.

If several preparative molecular sieve filtrations are performed in sequence, graduated separation limits can be selected. For example, a separation limit of 20,000 dalton can be used in a first filtration step and of 13,000 dalton in a second. This can be followed by an analytical molecular sieve filtration with upper and lower separation limits of 11,000 and 6,000 dalton. The exclusion limit of the gel used in all cases must be higher than about 10,000 dalton to allow a volume distribution of LR (molecular weight about 8500 dalton) between the stationary gel matrix phase and the mobile aqueous buffer phase.

The "exclusion limit" is a hydrodynamic parameter of a dissolved particle corresponding to the pore size of the gel matrix. Particles with a greater hydrodynamic parameter cannot penetrate the gel matrix (volume distribution coefficient $K_D=0$). The "separation limit" refers to a hydrodynamic parameter which has been chosen for the separation of dissolved particles from others, with values between the volume distribution coefficients $K_D=0$ and $K_D=1$.

For molecular sieve filtration the proteins are applied to the molecular sieve after solution in a protein-compatible liquid. A special example of a suitable solvent is 0.03 mol/l sodium-potassium phosphate solution containing 0.3 mol/l NaCl, 0.001 mol/l cysteine and having a pH of 6.5. After the filtration, the LR-containing fractions are collected. The dissolved proteins in the fractions are preferably concentrated by salting-out precipitation through addition or ammonium sulfate to a concentration of 3.7 mol/l (90% saturation). After separation of the precipitated proteins from the supernatant, they are again dissolved in a protein compatible liquid and, if necessary, subjected to a further purification step. Between the above-described purification steps, if necessary for special purposes at any stage, protein solutions can be separated and freed from unwanted salts by dialysis or ultra-filtration, e.g. against a protein-compatible liquid, preferably a sodium-potassium phosphate buffer. This is preferably achieved at membranes with an exclusion limit of about 500–1000 dalton. Small amounts of protein precipitates formed are removed by intermediary centrifugation to result in a clear protein solution. A desalting molecular sieve filtration on matrices with appropriate separation and exclusion limits can as well be used for this purpose, e.g. on Sephadex G10, G15 or G20 as matrices. Furthermore, by selecting an appropriate mobile phase in the usual way, a usual molecular sieve filtration step can also be used concommitantly for this purpose.

In the molecular sieve filtration purification steps about 0.4 mol/l ammonium sulfate is preferably added to the protein solution. In contrast to higher concentrations of this salt, at this concentration ammonium sulfate exerts a strong salting-in effect on proteins. Thus, proteins are better kept in solution during the molecular sieve filtration. Moreover, ammonium sulfate prevents growth of microorganisms and inhibits certain enzymes. Hence, it contributes to stabilization of the LR structure which is important when chromatography is performed at higher temperature (above about 20° C.) and under non-sterile conditions. To prevent the sulfhydryl group oxidation, about 0.001 mol/l of cysteine is preferably added to protein solutions throughout.

The temperature and pH conditions during molecular sieve filtration are not particularly critical. If the native conformation of the proteins shall be preserved, an optimum temperature range is about 0° to 8° C., and preferably about 0° to 4° C. The preferred pH range is between 6 and 9.

Use of above-mentioned separation processes according to the inventions achieves separation of a major part of the LR-accompanying foreign proteins from the LR mediator to be isolated, already prior to chromatography on hydroxyapatite. For example, according to one of the preferred embodiments, using fractional elution, two preparative and one analytical molecular sieve filtrations in sequence applied on the crude serum protein concentrate fraction, the volume of protein solution of 100 liters of initial crude contact-activated serum (corresponding to about 35 liters of wet protein mass, or 7–8 kg of dry protein mass) can be reduced to less than about 100 to 200 ml prior to chromatography on hydroxyapatite. It is obvious that this method for the first time allows preparation of larger, biotechnical amounts of LR. The quantity of protein to be chromatographed on hydroxyapatite is relatively small and already enriched in LR. Hydroxyapatite columns with total adsorbtion capacity for the intermediary product thus obtained ("crude LR preparation") from up to 2000 liters of contact-activated crude serum can still be processed within a normal laboratory.

(C.) ISOLATION OF THE HIGHLY PURIFIED LR PREPARATION BY CHROMATOGRAPHY ON HYDROXYAPATITE. FURTHER PURIFICATION OF THE PREPARATION TO MOLECULAR HOMOGENEITY AND CRYSTALLIZATION OF LR IN BIOLOGICALLY SPECIFIC, ACTIVE FORM.

After performance of one or of a combination of the separation processes described in Section B the resulting protein solution, in which LR is already enriched, is chromatographed on hydroxyapatite. This further separates other foreign proteins and leads to a highly purified LR preparation.

Ammonium sulfate and other salts, especially phosphates in the concentrated solution from the last, preceding separation step (crude LR preparation) must be removed in the described manner, preferably by dialysis or ultrafiltration at a membrance with an exclusion limit of about 500–1000 dalton prior to application of protein solution to the hydroxyapatite column. Apart from viscosity increase by accompanying salts, however, only the phosphate concentration of the protein solution is critical for the chromatography on hydroxyapatite. Furthermore, addition of NaCl, preferably 0.1 mol/l, specifically favours separation of eluted proteins from the hydroxyapatite column (effect on the $R_f$ value of eluting proteins without altering their other elution characteristics). The LR is eluted by a sodium-potassium phosphate concentration gradient, which preferably is linear. The LR-containing fractions are collected and then concentrated in one of the described manners, e.g. by addition of ammonium sulfate to a concentration of 3.7 mol/l and separation of precipitated proteins by usual methods.

The LR preparation obtained by chromatography on hydroxyapatite comprises about 900 mg protein from 100 liters of serum. In general, this protein mixture contains about 5% to 40% of LR. Thus, LR constitutes already a major portion in this purified product. However, if necessary, it may be further purified from residual contaminations by application of additional purification steps. Suitable further separation steps are analytical recycling or cascade molecular sieve filtration, re-chromatography on hydroxyapatite, zone-precipitation chromatography, analytical molecular sieve filtration, or combinations of these steps.

The recycling or cascade molecular sieve filtration can be performed under the conditions described above for the analytical molecular sieve filtration used to remove LR-accompanying foreign proteins before the chromatography on hydroxyapatite. The same molecular sieves and the same column conditions can be used. Sephadex G 50 as stationary matrix is preferred in a column of a length-to-diameter ratio of at least of about 50:1 and a maximum charge of about 3% of the column volume. The solvents used in the analytical molecular sieve filtration are also preferred as solvents for the elution in this method.

In recycling molecular sieve filtration, the distribution equilibria are disturbed continuously and the eluate is recycled onto the same column with fixed separation limits. In this way the separation length of the migrating protein distribution bands are differentially extended. Alternatively, in cascade molecular sieve filtration, distribution equilibria are disturbed by continuous transfer of the eluate into a new second column with the same or similar, defined parameters at fixed separation limits.

For the rechromatography on hydroxyapatite, the LR preparation is first freed from any foreign salts and ammonium sulfate, possibly present in the protein solution, preferably by dialysis or ultrafiltration at membranes with an exclusion limit of 500–1000 dalton. The resulting solution of the LR preparation is then applied onto the hydroxyapatite and eluted with the aid of a sodium-potassium phosphate concentration gradient. The fractions containing the LR are collected and concentrated in the usual way.

In the zone precipitation chromatography [cf. J. Porath, Nature, vol. 196 (1962), pp. 47–48], residual protein contaminations in the LR preparation are separated by salting-out fractionation of the proteins by means and along of a salt concentration gradient. Two variants of this technique for development of the chromatogram are known: Fractional precipitation zone chromatography and fractional elution zone chromatography. Both types of techniques may have selective advantages in distinct cases as described for fractional preciptation and fractional elution methods in protein separation. Temperature and pH, column dimensions, type of salt, shape of gradient, and column characteristics can all be varied within relatively wide limits.

The temperature for zone precipitation chromatography can be between 0° and 40° C. Preferably, a temperature range from about 0° to 10° C. is used, especially from about 4° to 6° C. The pH can be between 4 and 10; preferably, a pH range of 6 to 8 is used, especially a pH of about 7. The length-to-diameter ratio of the column used should be greater than about 10:1. A ratio of 30 to 100:1 and especially of about 50:1 is preferred. All protein-compatible salts having salting-out properties for proteins and LR are suitable. Examples of such salts are sodium-potassium phosphate, ammonium sulfate, and sodium sulfate. Ammonium sulfate is preferred.

The salt concentration gradient can have any desired shape provided that salting-out criteria of proteins achieve protein separation. Linear concentration gradients are preferred, especially an ascending linear concentration gradient from 25 to 80% ammonium sulfate saturation. The maximum column charge is about 5% and preferably about 1% of total column volume.

Analytical molecular sieve filtration for further purification of the LR preparation can be performed in the same manner as described for separation of LR-accompanying foreign proteins prior to chromatography on hydroxyapatite. The same molecular sieves, columns and performance conditions can be used.

A considerable separation of contaminating foreign proteins still present in the LR preparation can already be achieved by one of the above mentioned, additional purification steps. For example, by rechromatography on hydroxyapatite, a LR preparation is obtained in which LR is contained to about 50 to 70% of total protein present. Zone precipitation chromatography increases the LR fraction of the LR-preparation to about 98%, and further single analytical molecular sieve filtration increases it to about >99%. If only one additional purification step is performed, zone-precipitation chromatography is preferred.

The basic principle of separation of proteins in zone-precipitation chromatography are different, structure-related reversible solubility characteristics of proteins. They belong to the most sensitive molecular separation criteria and are often used for demonstration of molecular homogeneity of a protein. This explains preference of zone-precipitation chromatography over the various types of rechromatography methods, in which purification effects are based on optimum approximation to ideal equilibria in non-ideal polyelectrolyte systems.

For the therapeutic use, the LR preparation is preferably almost completely freed from contaminating foreign proteins by combination of at least two of the mentioned purification steps. Particularly preferred is a sequence of steps in which the LR preparation obtained by chromatography on hydroxyapatite is first subjected to analytical recycling molecular sieve filtration, then, rechromatographed on hydroxyapatite, further subjected to a zone precipitation chromatography, finally to an analytical molecular sieve filtration and then is crystallized. In another preferred embodiment, rechromatography on hydroxyapatite can also be performed after the zone-precipitation chromatography. In these preferred embodiments a LR preparation is obtained in which total protein content consists of up to more than 99% of LR.

The LR preparation is then in a molecularly homogeneous form according to all (chromatographic, electrophoretic, and solution) criteria available which characterize protein by molecular size, stability, charge and nature of surface; i.e. the LR solution then consists of a homogeneous, monodisperse protein phase.

As already stated, temperature and pH conditions are not particularly critical in most of the steps of the process in accordance with the invention. However, if the LR protein has to be obtained in its native conformation, separation and purification steps are carried out under almost physiological, reversible pH and salt conditions, and preferably at low temperatures with a maximum of about 10° C. and preferably 6° C. An essential advantage of the process in accordance with the invention is that these conditions can be easily verified.

The LR obtained can be stored in a buffered physiological saline, e.g. in 0.0015 mol/l sodium potassium phosphate solution containing 0.15 mol/l (0.9 w/v %) NaCl, 0.001 mol/l cysteine and having a pH of 7.4. After usual sterilization by filtration (pore diameter 0.2 μm), the protein preparation remains native and biologically active at room temperature for at least 200 h or frozen at −25° C. for at least 5 years. This stability of the protein can be considered also as one of the criteria of molecular homogeneity. The safe storage form at temperatures between −20° to +50° C. is the crystalline state of LR protein. In this form of a crystal suspension at high osmotic pressure, LR is protected against infection and degradation by microorganisms and bacterial growth.

For crystallization of LR, solid, powdered ammonium sulfate (ultrapure) is added to the sterile filtered LR-protein solution comprising 0.2 mol/l sodium-potassium phosphate buffer of pH 6.5, 10% glycerol, 0.2 mol/l NaCl, 0.001 mol/l cysteine, 0.1 mol/l KCl, and 20 mg/ml LR at 20° C. until the solution becomes slightly opalescent due to salting-out precipitation of LR. The slight protein precipitate is removed by high-speed centrifugation (16,000×g for 5 min). Further addition of few saturated ammonium sulfate solution at constant temperature forms a precipitate of double-refractive, optically anisotropic LR crystals in the clear solution. They grow slowly if left to stand for about a month between 0° to 20° C. Slow increase of concentration of ammonium sulfate favours LR crystal growth. Solution of LR crystals have the same molecular properties as the LR solution prior to crystallization. Physiological solutions of LR can be obtained from LR crystal suspension by salt exchange, e.g. by dialysis or ultrafiltration in the usual way at membranes with an exclusion limit of 500–1000 dalton.

The invention will now be given in detail by examples describing the isolation of the leukorecruitin protein preparation starting from porcine blood. However, in terms of the species used, the invention is not restricted to this form of embodiments.

EXAMPLE A

Preparation of leukorecruitin in serum. Regulated and limited proteolsysis of the serum by contact activation. Separation of the LR-containing crude serum protein concentrate fraction from other serum constituents, and preparation of a LR-containing crude serum protein concentrate fraction Production of LR in serum by contact activation, separation of the crude serum protein cencentrate fraction from other serum constituents, and preparation of a LR-containing crude serum protein concentrate fraction are explained. Unless otherwise specified, all procedures are carried out at 0° to 8° C. The centrifugation is performed as described, either on a one-step or two-step procedure (as flow-through centrifugation).

300 liters of porcine blood are coagulated without additives at room temperature. The blood clot is removed from the crude serum by filtration or decantation. The supernatant serum is separated from the remaining blood clot residues by centrifugation at 4° C. and 1000×g for 30 min. The clear serum (120 liters) is then immediately mixed with 5 mg granulated, insoluble, gel-swellable dextran per ml serum, or with 100 mg boiled and washed baker's yeast per ml serum and incubated in a water bath for 1 h at 37° C. under continuous stirring. The mixture is then cooled to 4° C. and the contact agent is removed by centrifugation. The presence of LR in the 120 liters of contact-activated serum obtained, containing about 9.2 kg of protein, can be demostrated by one of the assays described (biological method: leucocytosis reaction in vivo; mobilization of the bone-marrow leukocytes in vitro; physico-chemical method: by immunodiffusion and immunoelectrophoresis with anti-LR immunoglobulin fractions).

Unless otherwise specified, the following purification techniques are then performed in the presence of 0.001 mol/l cysteine at a temperature of 0° to 8° C.: 120 liters of contact-activated serum are adjusted to pH 4.5 with 5 mol/l acetic acid and mixed with 240 liters of 0.001 mol/l potassium phosphate-acetate buffer containing 0.2 mol/l NaCl and having a pH of 4.5. Then, 3 volume parts of the protein solution obtained are mixed by stirring in 1 volume part of swollen, regenerated cation exchanger (Na+ as mobile exchangeable counter-ion) coupled to a dextran matrix cross-linked by epichlorohydrin (CM-Sephadex C-50). The ion exchanger used has been pretreated for at least 1 day with porcine serum for surface inactivation, regenerated prior to use, and equilibrated with the mentioned phosphate-acetate buffer of pH 4.5.

The resulting mixture is stirred for about 24 h. The ion exchange gel is then settled and separated from the supernatant by filtration on a Büchner funnel. The gel is washed with three 120-liter portions of 0.001 mol/l potassium hydrogen phosphate-acetate buffer containing 0.2 mol/l NaCl, 0.001 mol/l cysteine and having a pH of 4,5, until the extinction of the filtrate at 280 nm is $E \leq 1.0$.

For elution of the LR-containing adsorbed proteins, the charged ion exchange gel is suspended three times in the same volume part of 0.5 mol/l potassium phosphate buffer at pH 6.5. The ion exchange gel is separated from the solution each time by centrifugation or filtration. The protein solutions obtained are combined (360 liters). The combined eluates of the cation-exchange gel are adjusted to a concentration of ammonium sulfate of 90% saturation by addition of 630 g of ammonium sulfate per liter eluate protein solution. During addition, the pH of the protein solution is checked continuously and maintained between 6.5 and 7.0 by addition of 2 mol/l ammonia. LR precipitates from the solution together with the majority of serum proteins. The protein precipitate is separated from the almost protein-free supernatant salt solution by centrifugation for 1 hr at 10,000×g. 49 liters of ammonium sulfate-containing protein mud are obtained, containing about 3.5 kg of protein (crude serum protein concentrate fraction).

EXAMPLE B

Crude purifiaction of LR: Separation of the bulk of the accompanying foreign proteins from LR. Preparation of a "crude LR-preparation"

EXAMPLE B1

Crude separation of LR by fractional elution of contaminating foreign proteins

For fractional elution, 49 liters of the crude serum protein concentrate fraction obtained as a mud as described above under example A, having an ammonium sulfate concentration of about 3.7 mol/l (90% saturation) are treated with 0.001 mol/l sodium-potassium phosphate buffer containing 0.1 mol/l NaCl, 0.001 mol/l cysteine and having a pH of 6.3 in quantities of 0.4 volume parts per volume part of crude serum portein concentrate fraction mud under stirring for about 24 h. Then, the residual insoluble protein precipitate which contains almost all LR is separated from the supernatant eluate by centrifugation at 10,000×g. About 70% (2.7 kg protein) of the starting crude serum protein concentrate fraction remain in the form of a mud (volume: about 14 liters). For removal of ammonium sulfate, this protein mud representing a crude LR-preparation is dialysed at a membrane with an exclusion limit of 500–1000 dalton against 0.001 mol/l sodium-potassium phosphate solution containing 0.1 mol/l NaCl, 0.001 mol/l cysteine and having a pH of 7.4 40 liters of ammonium sulfate-free protein solution are obtained and applied to a hydroxyapatite column according to Example C.

EXAMPLE B2

Crude separation of LR by fractional precipitation of contaminating foreign proteins For fractional precipitation, 49 liters of the crude serum protein concentrate fraction obtained as a mud as described above under Example A, are dissolved in a minimum volume of 0.01 ammonium acetate buffer containing 0.2 mol/l NaCl and having a pH of 5.0. One volume part of the resulting protein solution is adjusted to pH 4.0 with glacial acetic acid under stirring. Then, it is mixed with 0.2 volume parts of 96% ethanol at a temperature of 0° C. During addition of ethanol, the temperature and the pH are maintained constant. The mixture is stirred for 1 h at 0° C. 70% (2.45 kg) of foreign proteins present in solution are precipitated and separated from LR-containing supernatant protein solution by centrifugation for 1 h at least $16,000 \times g$. The separated precipitate of foreign proteins (10 liters) is washed four times with an equal volume of 0.01 mol/l ammonium acetate buffer containing 0.2 mol/l NaCl, 200 ml ethanol per liter buffer and having a pH of 4.0, at a temperature of 0° C. The washing solutions are combined with the main, first LR-containing supernatant protein solution and the mixture is adjusted to pH 5.0 using 2 mol/l ammonia. Then, the ethanol is separated off by lyophilization, molecular sieve filtration, or dialysis (exclusion limit 500–1000 dalton) against the ammonium acetate buffer. If dialysis or molecular sieve filtration have been used, the proteins are precipitated in the obtained alcohol-free solution by the addition of ammonium sulfate (90% saturation). They are separated from the almost protein-free supernatant salt solution by centrifugation at $10,000 \times g$ (45 min). The protein residue obtained by lyophilization or precipitation (1.05 kg protein) which represents a crude LR-preparation, is freed from ammonium sulfate and other salts by dialysis as given in Example B1. The dialyzed protein solution obtained can be applied onto the hydroxyapatite column as an ammonium sulfate-free solution (volume 16 liter) as described in Example C2.

EXAMPLE B3

Crude separation of LR from contaminating foreign proteins by preparative molecular sieve filtration For preparative molecular sive filtration, 1 volum part (49 liters) of crude serum protein precipitate fraction obtained as a mud as described above under Example A, is dissolved in 2 volume parts of 0.03 mol/l sodium-potassium phosphate solution containing 0.3 mol/l NaCl, 0.001 mol/l cysteine and having a pH of 6.7. The solution is centrifuged for 30 min at 4° C. and $10,000 \times g$, for removal of small amounts of insoluble particles. Then, the clear solution (147 liters) is subjected to a preparative molecular sieve filtration. It is applied to a column packed with a molecular sieve matrix of dextran cross-linked with epichlorohydrin (Sephadex G-50; particle size 50 to 150 $\mu$m). The column has a 10-fold volume of the protein solution volume and a length-to-diameter ratio of 10:1. The column is eluted with ascending flow (rate 3 cm/h) with 0.03 mol/l sodium potassium phosphate buffer containing 0.3 mol/l NaCl, 0.001 mol/l cysteine, 0.4 mol/l ammonium sulfate and having a pH of 6.7. The amount of buffer used for elution corresponds to the total column volume. The eluate is divided into two fractions with a separation limit of 20,000. The fraction with molecular weights larger than 20,000 dalton contains 85% of the initial foreign protein mass. The LR-containing fraction (0.5 kg of protein) with molecular weights smaller than 20,000 dalton is collected and constitutes the crude LR-preparation. The proteins of this fraction are concentrated as given in Example B2 by precipitation with ammonium sulfate and then, removal of ammonium sulfate by dialysis as given in Example B1. The resulting solution which still contains 15% of the original protein mass (7.5 liters), has a volume of 22.5 liters and can be applied to the hydroxyapatite column as will be described in Example C.

EXAMPLE B4

Crude separation of LR from contaminating foreign proteins by a sequence of fractional elution and preparative molecular sieve chromatography 49 liters of the crude serum protein concentrate fraction obtained as a mud as described above in Example A, are fractionally eluted as given in Example B1. The resulting 14 liters of protein mud containing LR, are dissolved in sodium-potassium phosphate buffer as described in Example B3. The resulting solution is processed for chromatography on Sephadex G-50 as described in Example B3. The fraction with molecular weights smaller than 20,000 dalton is collected, concentrated with ammonium sulfate according to Example B2, and finally dialysed according to Example B1. 6.0 liters of ammonium sulfate-free protein solution is obtained with a protein content of 0.4 kg, representing a crude LR-preparation. This solution can be further processed as given in Example C.

EXAMPLE B5

Crude separation of LR from contaminating foreign proteins by a sequence of fractional precipitation and preparative molecular sieve chromatography 49 liters of the crude serum protein concentrate fraction obtained as a mud as given in Example A are treated with ethanol for fractional precipitation of foreign proteins as given in Example B2. The protein residue obtained after removal of ethanol and concentration of proteins from the supernatant solution (1.05 kg of protein) then is dissolved and chromatographed on a molecular sieve as given in Example B3. 2.3 liters of ammonium sulfate-free protein solution are obtained, with a protein content of 160 g representing a crude LR-preparation.

EXAMPLE B6

Crude separation of LR from contaminating foreign proteins by a sequence of fractional elution, two preparative and one analytical molecular sieve filtrations 49 liters of the crude serum protein concentrate fraction obtained as mud as described above in Example A are fractionally eluted and then subjected to a preparative molecular sieve filtration as described in Example B4.

After concentration of proteins of the LR-containing fraction with a molecular weight smaller than 20,000 daltons by salting-out precipitation with ammonium sulfate according to Example B2, the obtained LR-containing protein precipitate is dissolved in 0.03 mol/l sodium-potassium phosphate buffer containing 0.3 mol/l NaCl, 0.001 mol/l cysteine and having a pH of 6.7. 1.5 volume parts of buffer per volume part of protein precipitate mud are used. A small amount of residual insoluble material is centrifuged off (10000×g, 1 h). For preparative molecular sieve rechromatography the solution is applied to a column packed with a molecular-sieve matrix of dextran cross-linked with epichlorohydrin (Sephadex G-50; particle size 50 to 150 μm). The column has a 10 fold volume of the protein solution and a length-to-diameter ratio of 10:1. The column is eluted in ascending mode at 3 cm/h with 0.03 mol/l sodium-potassium phosphate buffer containing 0.3 mol/l NaCl, 0.001 mol/l cysteine, 0.4 mol/l ammonium sulfate and having a pH of 6.7. The resulting eluate is divided into three fractions with separation limits larger than 20,000, smaller than 13,000 dalton and an intermediate fraction. The LR-containing protein fraction with a molecular weight range smaller than 13,000 dalton contains 130 g of protein and represents a crude LR-preparation. It is adjusted to an ammonium sulfate concentration of 3.7 mol/l for salting-out precipitation of proteins according to Example B2. The protein precipitate is separated from the supernatant by centrifugation.

The LR containing protein precipitate obtained is dissolved in 1,5 volume parts of the buffer solution with ammonium sulfate omitted as described above in the preceding molecular sieve filtration. The solution is centrifuged for 1 h at 10,000×g to remove a small quantity of insoluble residue.

For analytical molecular sieve filtration, the obtained clear LR-containing solution is applied to a column packed with a moleculr sieve matrix of dextran cross-linked with epichlorohydrin (Sephadex G-50) with a particle size of 20 to 80 μm. The column used has a 50-fold volume of the protein solution and a length-to-diameter ratio of 50:1. For elution in ascending mode (3 cm/h), a 0.03 mol/l sodium-potassium phosphate buffer containing 0.3 mol/l NaCl, 0.001 mol/l cysteine, and 0.4 mol/l of ammonium sulfate with a pH of 6.7 is used. The resulting eluate is divided into several fractions, the leukocytosis-inducing and leukocyte-mobilizing activities of which are tested. An intermediate fraction with a molecular weight range of 11,000 to 6000 dalton, containing essentially all LR and representing a crude LR-preparation is separated off. This fraction is adjusted to an ammonium sulfate concentration of 3.7 mol/l for salting-out precipitation of proteins according to Example B2. The precipitated proteins are removed from the supernatant by centrifugation (10000×g, 1h). They can be dissolved as described in the preceding steps or, preferentially, as given in Example C1. A small amount of insoluble material is removed by usual centrifugation. Yield: 180 ml of clear concentrated LR-containing protein solution with a protein content of 9.0 g.

FIGS. 6 to 8 show the course of the separation of the crude LR-preparation from the accompanying contaminating foreign preteins by a sequence of two preparative and one analytical molecular sieve filtration in form of chromatograms.

EXAMPLE B7

Crude separation of LR from contaminating foreign proteins by a sequence of fractional elution, fractional precipitation, one preparative and one analytical molecular sieve filtration processes 49 liters of the crude serum-protein concentrate fraction obtained as a mud as descrived in Example A are treated sequentially for fractional elution (Example B1; result: 14 liters of protein mud) and for fractional precipitation of foreign proteins (Example B2). After removal of ethanol and concentration of soluble proteins of the supernatant solution, the protein residue obtained (1.05 kg of protein) is subjected to one preparative molecular sieve filtration and, then sequentially to an analytical molecular sieve filtration, both described in Example B6. The same result for the crude LR-preparation as in Example B6 is obtained.

EXAMPLE B8

Crude separation of LR from contaminating foreign proteins by a sequence of fractional precipitation, two preparative and one analytical molecular sieve filtration processes 49 liters of the crude serum-protein concentrate fraction obtained as a mud as described in Example A, are first treated sequentially with ethanol for fractional precipitation of foreign proteins and subjected to a preparative molecular sieve filtration as described in Example B5. The protein residue obtained after concentration (160 g of protein) is dissolved as described and then subjected as given in Example B6 to a sequence of the second preparative and to the analytical molecular sieve filtration. The same result for the crude LR-preparation as in Example B6 is obtained.

EXAMPLE B9

Crude Separation Of LR From Containing Foreign Proteins By Calcium Phosphate Gel Treatment 0.49 liter of the crude serum protein concentrate fraction obtained as a mud as described in Example A) is dissolved in a minimum volume of 0.001 mol/l sodium-potassium phosphate solution containing 0.2 mol/l NaCl, 0.001 mol/l cysteine and having a pH of 6.6. The solution is centrifuged for 30 min. at 16,000×g for removal of small quantities of insoluble material. The solution is then freed from ammonium sulfate by dialysis for 24 h against 0.001 mol/l sodium-potassium phosphate buffer containing 0.1 mol/l NaCl, 0.001 mol/l cysteine and having a pH of 6.6, at a membrane with an exclusion limit of 500 to 1000 dalton, until sulfate ions are no longer detectable. 60 ml of calcium phosphate gel equilibrated with the above-described sodium-potassium phosphate buffer is then stirred into the LR-containing protein solution. The mixture obtained is further stirred for 1h. The gel is then removed by centrifugation for 5 min. at 10000×g and washed three times with the above mentioned sodium-potassium phosphate buffer at pH 6.6. The gel is three times again suspended in a minimum volume of buffer solution and separated again by centrifugation. All the LR-and protein-containing solutions are then combined and proteins precipitated and concentrated by the addition of ammonium sulfate. The LR-containing protein precipitate is dissolved (about 30 g of protein) and concomitantly freed from the ammonium sulfate by dialysis as given in Example B1. It can then be applied as an ammonium-sulfate free solution to the hydroxyapatite column as in C).

EXAMPLE B10

Crude Separation Of LR From Contaminating Foreign Proteins By Anion Exchange Adsorption 0.49 l of the curde serum protein concentrate fraction obtained as a mud as described in Example A is dissolved in a minimum volume of 0.01 mol/l tris-HCl solution containing 0.03 mol/l NaCl, 0.001 mol/l cysteine and having a pH of 8.0. A small amount of insoluble material is removed by centrifugation as described. The solution is dialysed at a membrane with an exclusion limit of 500–1000 dalton against the mentioned buffer solution until sulfate ions are to longer detectable. 2 volume parts of a swollen and regenerated anion exchanger, DEAE-Sephadex A-50, equilibrated with the above buffer system, are then added to one volume part of the above mentioned clear LR-containing protein solution with continued stirring.

The mixture obtained is stirred for 5 h. The ion exchanger gel is settled and separated from the supernatant protein solution by filtration on a Büchner funnel. The gel is then washed with three 4-1 portions of the above-described adsorption buffer until the extinction of the filtrate at 280 nm is $\leq 1.0$.

For elution of LR and the other adsorbed proteins, one volume part of the charged ion exchanger gel is three times suspended with stirring in 2 volume parts of 0.01 mol/l piperazine-HCl buffer, containing 2.0 mol/l NaCl, 0.001 mol/l cysteine and hving a pH of 6.5. The ion exchanger gel is separated from supernatant solutions by decantation, filtration (on a Büchner funnel), or centrifugation. The LR-containing protein solutions obtained are combined (6 l) and proteins are concentrated in one of the usual, described manner, preferably by salting-out precipitation with ammonium sulfate as described in Example B2. The resulting protein precipitate (about 25 g of protein) is freed from ammonium sulfate by dialysis as given in Example B1 and can be applied as an ammonium sulfate-free solution onto the hydroxyapatite column as presented in Example C.

EXAMPLE C.

Isolation Of A Highly Purified LR-Preparation By Chromatography On Hydroxyapatite. Further Purification Of The Preparation To Molecular Homogeneity And Crystallization Of LR In Biologically Specific, Active Form

EXAMPLE C1

Chromatography Of The Crude LR-Preparation B6 On Hydroxyapatite

The crude LR-protein precipitate obtained in Example B6 is dissolved in a minimum volume of 0.0015 mol/l sodium-potassium phosphate buffer containing 0.15 mol/l NaCl and 0.001 mol/l cysteine, pH 7.4. A small amount of residual insoluble material is discarded after separation by centrifugation (10,000×g, 1h, 4° C.). The clear solution is dialysed, ultrafiltered, or desalted by molecular sieve filtration (exclusion limit: 500–1000 dalton) against 0.001 mol/l sodium-potassium phosphate buffer containing 0.01 mol/l NaCl, 0.001 mol/l cysteine and having a pH of 7.4, until no sulfate is any more detectable (with $BaCl_2$) in the solution. A small fraction of insoluble material is removed by centrifigation for 1 h at 10,000×g and 40° C.

The clear LR-containing protein solution obtained (180 ml; protein content: 9.0 g) is applied to a column packed with hydroxyapatite. The column has a length-to-diameter ratio of 10:1 and 3-fold volume of the protein solution volume to be applied (45 mg protein/ml). Prior to application of the LR-preparation, the column is first equilibrated with a 5-fold volume of 0.001 mol/l sodium-potassium phosphate buffer containing 0.1 mol/l NaCl, 0.001 mol/l cysteine and having a pH of 7.4 (flow rate 3cm/h).

The negatively adsorbing proteins are washed out by elution with the buffer solution used to equilibrate the column. Then, elution of the LR-containing fraction is performed within 4 days with a linear phosphate concentration gradient of 0.001 mol/l to 0.5 mol/l of sodium-potassium phosphate buffer of pH 7.4, having the given constant NaCl and cysteine concentrations. The elution gradient is measured by conductivity. The LR is eluted at a mean phosphate concentration of 0.04 mol/l and thus is separated from the most other proteins as well. A usual step (salting-out precipitation or ultrafiltration) for concentration of active fractions is applied. A suitable buffer for dissolving the protein concentrate is 0.001 mol/l sodium-potassium phosphate buffer containing 0.001 mol/l cysteine and having a pH of 7.2. Thus, it is possible to adjust to any other salt concentration by addition of a small volume of a concentrated salt solution. For example, if required, addition of 0.05 volume parts of 2 mol/l NaCl solution of pH 7.2 results a phosphate buffered LR-containing protein solution with 0.1 mol/l NaCl. A protein solution volume of 20 ml is obtained. It contains about 900 mg protein with an LR-content of about 5 to 40% of total protein.

The isolation of the purified LR-preparation by chromatography on hydroxyapatite as described in Example C1 is shown in the chromatogram of FIG. 9.

EXAMPLE C2

Chromatography Of The Crude LR-Preparation B2 On Hydroxyapatite.

Example C1 is repeated with the crude, LR-containing protein precipitate obtained as described in Example B2. According to the description given in Example B2, after dialysis and removal of a small fraction of insoluble proteins, 16 liters of clear protein solution are obtained and applied to a column packed with hydroxyapatite with characteristics as given in Example C1 (volume 3×16 liters, length-to-diameter ratio 10:1); i.e. with a diameter of 18 cm and a length of 180 cm. After elution, about 1200 mg of purified product is obtained, which has an LR-portion of about 5–10% of total protein content.

EXAMPLE C3

Further Processing Of The Purified Product C1 To A Highly Purified LR-Preparation By Zone-Precipitation Chromatography The LR-preparation obtained as given in Example C1 is dissolved in 0.1 mol/l sodium-potassium phosphate solution containing 0.1 mol/l NaCl, 0.001 mol/l cysteine, 1 mol/l of ammonium sulfate and having a pH of 7.4 to result a protein concentration of about 45 mg/ml. At a temperature of 4° C., the solution obtained (20 ml) is applied to a column packed with a molecular-sieve matrix of dextran cross-linked with epichlorohydrin (Sephadex G-50). The matrix is equilibrated with an ascending linear ammonium sulfate concentration gradient of 1.0 to 3.2 mol/l (25 to 80% saturation) ammonium sulfate. The gradient corresponds to a +2% increase in the ammonium sulfate concentration per cm of column length (+0.08 mol/l ammonium sulfate per cm). The gradient ranges over half of the column length. Thus, the other half of column length is equilibrated with the buffer containing a a constant concentration of 3.2 mol/l ammonium sulfate.

The length-to-diameter ratio of the column is 50:1, and the column has 100 fold volume of the solution applied. The flow rate is 2 cm/h.

Protein elution from the column is carried out with the above described sodium-potassium phosphate buffer containing 1 mol/l of ammonium sulfate. The active fractions which elute at 61% ammonium sulfate saturation, are collected and the proteins are concentrated in the usual manner (salting-out precipitation or ultrafiltration).

For dissolving of the protein precipitates or concentrates obtained, a buffer as given in example C1 is preferably used (0.001 mol/l sodium-potassium phosphate buffer containing 0.001 mol/l cysteine and having a pH of 7.2). 340 mg (8 ml) of purified LR-preparation is obtained, consisting of 70% of LR of total protein content.

EXAMPLE C4

Further Processing Of Purified Product C1 To A Highly Purified LR-Preparation By A Sequence Of Analytical Recycling Molecular Sieve Filtration, Rechromatography On Hydroxyapatite, Zone-Precipitation And Analytical Molecular Sieve Chromatography.

The purified LR preparation obtained as given in Example C1 after concentration of proteins either by salting-out precipitation with ammonium sulfate or ultrafiltration at a membrane with an exclusion limit of 500–1000 dalton, or by lyophilization (900 mg; about 20 ml with 45 mg protein/ml) is dissolved in 0.003 mol/l sodium-potassium phosphate buffer containing 0.3 mol/l NaCl, 0.001 mol/l cysteine and having a pH of 7.4. A small fraction of insoluble proteins is then removed by centrifugation for 30 min at 48,000×g.

The clear LR-containing protein solution obtained is then subjected to an analytical recycling molecular weight filtration chromatography. The solution is applied onto a column packed with Sephadex G-50 with a particle size of 20 to 80 μm at a temperature of 4° C. The column has 50 times the volume of the protein solution and a length-to-diameter ratio of 50:1. Elution is performed by a 0.03 mol/l sodium-potassium phosphate buffer containing 0.3 mol/l NaCl, 0.001 mol/l cysteine, and 0.4 mol/l ammonium sulfate. The eluates are recycled three times at a separation limit of 9000 dalton.

After conventional protein concentration 810 mg of the LR-containing product with a molecular weight of 8500 dalton is obtained. It is dissolved in a minimum volume of 0.001 mol/l sodium-potassium phosphate buffer with 0.001 mol/l cysteine and a pH of 7.20.

The obtained LR-containing product is then chromatographed on a column packed with hydroxyapatite which is equilibrated with the latter-mentioned buffer system. The column has a length-to-diameter ratio of 20:1 and at least 5 times the volume of the protein solution (about 45 mg protein/ml). Elution is carried out within 6 days with a phosphate concentration gradient which is very flat and linear in the range of 0.001 to 0.1 mol/l sodium potassium phosphate. pH and cysteine concentration are kept constant. 405 mg of purified LR-preparation are obtained, which consist to about 50 to 70% of LR of total protein.

The LR preparation obtained as above is now subjected to a zone-precipitation chromatography as described in Example C3. 205 mg (5 ml) of further purified LR-preparation are obtained which consists of more than 98% of LR.

The LR-preparation resulting from zone-precipitation chromatography is finally subjected to an analytical molecular sieve filtration. For this purpose, the LR preparation is dissolved in 0.003 mol/l sodium-potassium phosphate buffer containing 0.3 mol/l NaCl, 0.001 mol/l cysteine and having a pH of 7.4. The resulting total volume of 5 ml protein solution contains about 35 to 45 mg/ml protein. The clear solution obtained is applied onto a column packed with Sephadex G-50 with a particle size of 20 to 80 μm. The column used has at least 50 times the volume of the protein solution and a length-to-diameter ratio of at least 50:1. A 0.03 mol/l sodium-potassium phosphate buffer, containing 0.3 mol/l NaCl, 0.001 mol/l cysteine, 0.4 mol/l ammonium sulfate and having a pH of 7.4 is used for elution of LR (flow rate 3 cm/h). After a conventional concentration step, 200 mg/5 ml of LR-preparation are obtained. It consists of more than 99% LR (yield about 10%).

The final purification of the LR as described in Example C4 is shown in the chromatograms of FIGS. 10 to 13.

Extensive desalting by dialysis, ultrafiltration, or molecular sieve filtation with an exclusion limit of 1000 dalton against a pyrogen-free physiological saline, e.g. 0.0015 mol/l sodium-potassium phosphate buffer, containing 0.15 mol/l NaCl (=0.9% NaCl), 0.001 mol/l cysteine and having a pH of 7.4, and sterilization by filtration (pore diameter 0.2μ) results a LR-preparation which can be used at appropriate concentration directly for biological, physiological, pharmacological, or biochemical purposes of for crystallization of LR. Vice versa, prior to use, the crystals can be dissolved by dialysis against the mentioned buffered physiological saline at a membrane with an exclusion limit of 1000 dalton.

What is claimed is:

1. A method for influencing the immune system of mammals comprising administering an effective amount of a pharmaceutical composition including substantially pure leukocytosis inducing and leukocyte recruiting protein, leukorecruitin, having the following biological effects:
   a. positive leukocytosis reaction and leukocyte recruitment from the bone marrow into the blood of animals and humans in vivo;
   b. positive leukocyte mobilization directly from the bone marrow in vitro;
and the following physico-chemical properties:
   a. molecular weight about 8,500 daltons;
   b. a single polypeptide chain;
   c. anodic electrophoretic migration at pH 7.4 in acrylamide matrices;
   d. soluble in aqueous media, including 20% ethanol at pH's between about 4 and 10;
   e. insoluble in $(NH_4)_2SO_4$ solutions having concentrations higher than 61%, corresponding to 2.5 mol $(NH_4)_2SO_4/l$;
   f. constant temperature coefficient of solubility in ammonium sulfate solutions between $-10°$ C. and $+50°$ C.;
   g. crystallizes in the form of double-refractive, optionally anisotopic crystals from ammonium sulfate solutions at ammonium sulfate concentrations higher than 61%;
   h. insoluble in chloroform, benzene, xylene and other apolar non-aqueous and water-immiscible solvents;

i. denatures in chloroform, benzene and xylene resulting in destruction of conformational structure and loss of biological activity;
j. contains tyrosine, tryptophan, phenylalanine, alanine, glycine, lysine, serine, valine, glutamic acid, arginine, and leucine;
k. adsorbs reversibily on anion and cation exchangers, calcium phosphate gels and hydroxyapatite and is capable in native form of volume-partition chromatography; and
l. possesses extinction coefficients according to Table I:

TABLE I

| Wavelength, nm | $E$1mg/ml, 1cm(H$_2$O,20° C.) ± 6% |
|---|---|
| 250 (min.) | 0.36 |
| 260 | 0.42 |
| 277 (max.) | 0.54 |
| 280 | 0.53 |
| 290 | 0.32 |
| 400–1000 | 0 |
| $E_{280}/E_{260}$ | 1.26 | and wherein said protein is substantially free of the following biologic properties:
a. increase of capillary permeability in the skin;
b. spasmogenic activity on smooth muscles;
c. spasmogenic activity on striated muscles;
d. significant endotoxin content or effects in animals and humans identical with or similar to those of endotoxins;
e. chemo attraction or chemotaxis of leukocytes in vitro;
f. positive or negative chemokinetic activity on leukocytes in vitro;
g. phagocytosis stimulating activity on leukocytes in vitro;
h. apparent shock or other detrimental systemic effect of immediate or protracted type in animals and humans in vivo;
i. pyrogenic activity in anaimals and humans in vivo;
j. lysis effects alone or in the presence of plasma or serum on erythrocytes, thrombocytes, and luekocytes in vitro;
k. phlogistic action in situ at reation sites of formation or application of leukorecruitin;
i. blood clot including activity alone or in presence of plasma;
m. aggregation of erythrocytes, thrombocytes and leukocytes alone, in salt solutions or in presence of plasma;
n. mitogenic activity on leukocytes in spleen, blood or bone marrow;
o. mitogenic activity on endothelial cells of arterial vessels in vivo and in vitro;
p. induction of vascularization of corneal tissues by chemotropism;
g. chalone activity on leukocytes in spleen and bone marrow; and
r. chalone activity on endothelia cells of arterial vessels.

2. The method of claim 1 wherein said pharmaceutical composition additionally includes a compatible carrier or vehicle.

3. A method for influencing the immune system in a mammal which comprises administering an effective amount of an antileukorecruitin immunoglobin.

4. A method for diagnosing hematological disorders comprising administering an effective amount of substantially pure leukorecruitin.

5. A method for diagnosing hematological disorders comprising administering an effective amount of antileukorecruitin immunoglobin.

6. A method for treating immunological disorders which comprises administering an effective amount of leukorecruitin and a suitable carrier.

7. A composition of matter for treating immunolgcial disorders consisting essentially of leukorecrutin and a suitable carrier.

8. A pharmaceutical composition for influencing the immune system in a mammal, comprising a therapeutically effective amount of a substantially pure leukocytosis indicuing and leukocyte recruiting protein (leukorecruitin) in a pharmaceutically acceptable carrier, said leukorecruitin having the following biological effects:
a. positive leukocytosis reaction and leukocyte recruitment from the bone marrow into the blood of animals and humans in vivo;
b. positive leukocyte mobilization directly from the bone marrow in vitro;
and the following physico-chemical properties:
a. molecular weight about 8,500 daltons;
b. a single polypeptide chain;
c. anodic electrophoretic migration at pH 7.4 in acrylamide matrices;
d. soluble in aqueous media including 20% ethanol at pH's between about 4 and 10;
e. insoluble in (NH$_4$)$_2$SO$_4$ solutions having concentrations higher than 61%, corresponding to 2.5 mol (NH$_4$)$_2$SO$_4$/l;
f. constant temperature coefficient of solubility in ammonium sulfate solutions between −10° C. and +50° C.;
g. crystallizes in the form of double-refractive, optionally anisotopic crystals from ammonium sulfate solutions at ammonium sulfate concentrations higher than 61%;
h. insoluble in chloroform, benzene, xylene and other apolar non-aqueous and water-immiscible solvents;
i. denatures in chloroform, benzene and xylene resulting in destruction of conformational structure and loss of biological activity; j. contains tyrosine, tryptophan, phenylalanine, alanine, glycine, lysine, serine, valine, glutamic acid, arginine, and leucine; k. adsorbs reversibly on anion- and cation-exchangers, calcium phosphate gels and hydroxyapatite and is capable in native form of volume-partition chromatography; and l. possesses extinction coefficients according to Table I:

TABLE I

| Wavelength, nm | $E$1mg/ml, 1cm(H$_2$O,20° C.) ± 6% |
|---|---|
| 250 (min.) | 0.36 |
| 260 | 0.42 |
| 277 (max.) | 0.54 |
| 280 | 0.53 |
| 290 | 0.32 |
| 400–1000 | 0 |
| $E_{280}/E_{260}$ | 1.26 | and wherein said protein is substantially free of the following biologic properties:
a. increase of capillary permeability in the skin;
b. spasmogenic activity on smooth muscles;
c. spasmogenic activity on striated muscles;

d. significant endotoxin content or effects in animals and humans identical with or similar to those of endotoxins;
e. chemo attraction or chemotaxis of leukocytes in vitro;
f. positive or negative chemokinetic activity on leukocytes in vitro;
g. phagocytosis stimulating activity on leukocytes in vitro;
h. apparent shock or other detrimental systemic effects of immediate or protracted type in animals and humans in vivo;
i. pyrogenic activity in animals and humans in vivo;
j. lysis effects alone or in the pressure of plasma or serum on erythrocytes, thrombocytes, and leukocytes in vitro;
k. phlogistic action in situ at reaction sites of formation or application of leukorecruitin;
l. blood clot inducing activity alone or in presence of plasma;
m. aggregation of erythrocytes, thrombocytes and leukocytes alone, in salt solutions or in presence of plasma;
n. mitogenio activity on leukocytes in spleen, blood or bone marrow;
o. mitogenic activity on endothelial cells of arterial vessels in vivo and in vitro;
p. induction of vascularization of corneal tissues by chemotropism;
q. chalone activity on leukocytes in spleen and bone marrow; and
r. chalone activity on endothelial cells of arterial vessels.

* * * * *